United States Patent
Galer et al.

(10) Patent No.: US 12,144,787 B2
(45) Date of Patent: *Nov. 19, 2024

(54) METHOD OF TREATING PATIENTS WITH A MUTATION IN CYCLIN-DEPENDENT KINASE-LIKE 5 (CDKL5)

(71) Applicants: ZOGENIX INTERNATIONAL LIMITED, Berkshire (GB); Karl Bozicevic, Redwood City, CA (US)

(72) Inventors: Bradley S. Galer, West Chester, PA (US); Bret Megargel, San Diego, CA (US)

(73) Assignee: Zogenix International Limited, Berkshire (GB)

( * ) Notice: Subject to any disclaimer, the term of this patent is extended or adjusted under 35 U.S.C. 154(b) by 301 days.

This patent is subject to a terminal disclaimer.

(21) Appl. No.: 17/289,125

(22) PCT Filed: Nov. 22, 2019

(86) PCT No.: PCT/IB2019/060067
§ 371 (c)(1),
(2) Date: Apr. 27, 2021

(87) PCT Pub. No.: WO2020/105005
PCT Pub. Date: May 28, 2020

(65) Prior Publication Data
US 2022/0008389 A1   Jan. 13, 2022

(51) Int. Cl.
| | | |
|---|---|---|
| A61K 31/137 | (2006.01) | |
| A61K 31/04 | (2006.01) | |
| A61K 31/05 | (2006.01) | |
| A61K 31/36 | (2006.01) | |
| A61P 25/08 | (2006.01) | |

(52) U.S. Cl.
CPC ............ *A61K 31/137* (2013.01); *A61K 31/04* (2013.01); *A61K 31/05* (2013.01); *A61K 31/36* (2013.01); *A61P 25/08* (2018.01)

(58) Field of Classification Search
CPC ...... A61K 31/137; A61K 31/05; A61K 31/36; A61K 31/04; A61P 25/08
See application file for complete search history.

(56) References Cited

U.S. PATENT DOCUMENTS

| | | |
|---|---|---|
| 3,117,160 A | 1/1964 | Holland |
| 3,198,833 A | 8/1965 | Beregi |
| 3,198,834 A | 8/1965 | Beregi et al. |
| 3,759,979 A | 9/1973 | Beregi et al. |
| 4,309,445 A | 1/1982 | Wurtman |
| 4,452,815 A | 6/1984 | Wurtman |
| 4,824,987 A | 4/1989 | Kleeman |
| 4,857,553 A | 8/1989 | Ward et al. |
| 5,587,398 A | 12/1996 | Elmaleh et al. |
| 5,808,156 A | 9/1998 | Cannata et al. |
| 5,811,586 A | 9/1998 | Cannata et al. |
| 5,834,477 A | 11/1998 | Mioduszewski |
| 5,985,880 A | 11/1999 | Chang |
| 6,045,501 A | 4/2000 | Elsayed et al. |
| 6,315,720 B1 | 11/2001 | Williams et al. |
| 6,561,976 B2 | 5/2003 | Elsayed et al. |
| 6,561,977 B2 | 5/2003 | Williams et al. |
| 6,599,901 B1 | 7/2003 | Flohr |
| 6,755,784 B2 | 6/2004 | Williams et al. |
| 6,869,399 B2 | 3/2005 | Williams et al. |
| 6,908,432 B2 | 6/2005 | Elsayed et al. |
| 7,141,018 B2 | 11/2006 | Williams et al. |
| 7,585,493 B2 | 9/2009 | Hale |
| 7,668,730 B2 | 2/2010 | Reardan et al. |
| 7,714,020 B2 | 5/2010 | Gluckman et al. |
| 7,765,106 B2 | 7/2010 | Reardan et al. |
| 7,765,107 B2 | 7/2010 | Reardan et al. |
| 7,797,171 B2 | 9/2010 | Reardan et al. |
| 7,874,984 B2 | 1/2011 | Elsayed et al. |
| 7,895,059 B2 | 2/2011 | Reardan et al. |

(Continued)

FOREIGN PATENT DOCUMENTS

| | | |
|---|---|---|
| CN | 1425167 | 6/2003 |
| CN | 1634857 A | 7/2005 |

(Continued)

OTHER PUBLICATIONS

Gursoy et al. (Mar. 2016), Diagnostic Approach to Genetic Causes of Early-Onset Epileptic Encephalopathy, Journal of Child Neurology, 31, 523-532 (Year: 2016).*
Naegelin et al., (May 22, 2015), OP24-2321 FINGORETT—An ongoing phase I clinical study to assess safety and efficacy of oral fingolimod (FTY720) in children with Rett syndrome, European Journal of Paediatric Neurology, 19, p. S8. (Year: 2015).*
Mangatt et al., (2016, Prevalence and onset of comorbidities, Orphanet Journal of Rare Diseases 2, 1-17 (Year: 2016).*
Patani et al. (Dec. 19, 1996) Bioisosterism A rational approach in drug design, Chem. Rev., 96, 3147-3176 (Year: 1996).*
Naegelin et al., (May 22, 2015), OP24-2321 FINGORETT—An ongoing phase I [. . . ], European Journal of Paediatric Neurology, 19, p. S8 (Year: 2015).*
Abraham et al., (1971, Relationship of Childhood Weight Status to Morbidity in Adults, HSMHA Health Reports, 86, 273-284). (Year: 1971).*

(Continued)

*Primary Examiner* — Kortney L. Klinkel
*Assistant Examiner* — Dawanna Shar-Day White
(74) *Attorney, Agent, or Firm* — Bret E. Field; Bozicevic, Field & Francis LLP

(57) ABSTRACT

A method of treating and/or preventing symptoms of Rett syndrome (RTT) in a patient such as a patient previously diagnosed with Rett syndrome, by administering an effective dose of a 5-$HT_{1D}$, 5-$HT_{2A}$, 5-$HT_{2C}$ or sigma-1 receptor agonist (e.g., fenfluramine or its pharmaceutically acceptable salt) to that patient. RTT patients are treated at a preferred dose of less than about 1.0 mg/kg/day and may be administered as fenfluramine in an amount of between 0.2 to 0.8 mg/kg/day, to a maximum of 30 mg/day in a liquid oral dose.

17 Claims, No Drawings

(56) References Cited

U.S. PATENT DOCUMENTS

| | | |
|---|---|---|
| 7,959,566 B2 | 6/2011 | Williams et al. |
| 8,204,763 B2 | 6/2012 | Elsayed et al. |
| 8,263,650 B2 | 9/2012 | Cook et al. |
| 8,315,886 B2 | 11/2012 | Williams et al. |
| 8,386,274 B1 | 2/2013 | Pinsonneault |
| 8,457,988 B1 | 6/2013 | Reardan et al. |
| 8,589,182 B1 | 11/2013 | Reardan et al. |
| 8,589,188 B1 | 11/2013 | Elsayed et al. |
| 8,626,531 B2 | 1/2014 | Williams et al. |
| 8,731,963 B1 | 5/2014 | Reardan et al. |
| 9,125,900 B2 | 9/2015 | Meyer |
| 9,549,909 B2 | 1/2017 | Ceulemens |
| 9,603,814 B2 | 3/2017 | Ceulemens |
| 9,603,815 B2 | 3/2017 | Ceulemens |
| 9,610,260 B2 | 4/2017 | Ceulemens |
| 10,351,509 B2 | 7/2019 | Londesbrough |
| 10,351,510 B2 | 7/2019 | Londesbrough |
| 10,452,815 B2 | 10/2019 | Stewart et al. |
| 10,478,441 B2 | 11/2019 | Ceulemens |
| 10,478,442 B2 | 11/2019 | Ceulemens |
| 10,517,841 B1 | 12/2019 | Galer et al. |
| 10,603,290 B2 | 3/2020 | Farr |
| 10,682,317 B2 | 6/2020 | Abu-Izza |
| 10,689,324 B2 | 6/2020 | Farr |
| 10,947,183 B2 | 3/2021 | Londesbrough et al. |
| 10,950,331 B2 | 3/2021 | Stewart et al. |
| 10,952,976 B2 | 3/2021 | Galer |
| 11,040,018 B2 | 6/2021 | Farr |
| 11,325,882 B2 | 5/2022 | Farr |
| 11,352,882 B2 | 5/2022 | Farr |
| 11,406,606 B2 | 8/2022 | Farr |
| 11,458,111 B2 | 10/2022 | Abu-Izza |
| 11,571,397 B2 * | 2/2023 | Martin ................ A61K 31/137 |
| 11,612,574 B2 | 3/2023 | Galer |
| 11,634,377 B2 | 4/2023 | Londesbrough et al. |
| 11,673,852 B2 | 6/2023 | Farr |
| 11,759,440 B2 | 9/2023 | Farr |
| 11,786,487 B2 | 10/2023 | Farr |
| 11,949,918 B2 | 4/2024 | Li et al. |
| 2002/0038310 A1 | 3/2002 | Reitberg |
| 2002/0098175 A1 | 7/2002 | Zohoungbogbo |
| 2003/0007934 A1 | 1/2003 | Rabinowitz et al. |
| 2003/0118654 A1 | 5/2003 | Santos et al. |
| 2004/0117205 A1 | 6/2004 | Reardan et al. |
| 2004/0249212 A1 | 12/2004 | Smallridge et al. |
| 2005/0182103 A1 | 8/2005 | Finke et al. |
| 2005/0260610 A1 | 11/2005 | Kurtz et al. |
| 2006/0121066 A1 | 6/2006 | Jaeger et al. |
| 2006/0270611 A1 | 11/2006 | Dries et al. |
| 2007/0123556 A1 | 5/2007 | Pennypacker |
| 2008/0004904 A1 | 1/2008 | Tran |
| 2008/0103179 A1 | 5/2008 | Tam |
| 2008/0243584 A1 | 10/2008 | Srinivasan |
| 2008/0261962 A1 | 10/2008 | Greer |
| 2009/0171697 A1 | 7/2009 | Glauser |
| 2010/0088778 A1 | 4/2010 | Mulley |
| 2010/0298181 A1 | 11/2010 | Hanada et al. |
| 2011/0092535 A1 | 4/2011 | Barnes et al. |
| 2011/0184747 A1 | 7/2011 | Bozic |
| 2011/0212171 A1 | 9/2011 | Venkatesh et al. |
| 2011/0230473 A1 | 9/2011 | Gordon et al. |
| 2012/0065999 A1 | 3/2012 | Takatoku |
| 2012/0107396 A1 | 5/2012 | Khan |
| 2012/0115958 A1 | 5/2012 | Mariotti et al. |
| 2012/0157392 A1 | 6/2012 | Martin et al. |
| 2012/0270848 A1 | 10/2012 | Mannion |
| 2012/0303388 A1 | 11/2012 | Vishnubhatla |
| 2013/0079336 A1 | 3/2013 | Mott et al. |
| 2013/0218586 A1 | 8/2013 | Huser |
| 2013/0296398 A1 | 11/2013 | Whalley |
| 2014/0030343 A1 | 1/2014 | Lamson |
| 2014/0142140 A1 | 5/2014 | Bird |
| 2014/0162942 A1 | 6/2014 | Ghosal |
| 2014/0329908 A1 | 11/2014 | Ceulemens et al. |
| 2014/0343044 A1 | 11/2014 | Ceulemens et al. |
| 2014/0343162 A1 | 11/2014 | Ceulemens et al. |
| 2014/0348966 A1 | 11/2014 | Balemba |
| 2015/0080377 A1 | 3/2015 | Dhanoa |
| 2015/0291597 A1 | 10/2015 | Mannion |
| 2015/0310187 A1 | 10/2015 | Rabinowitz |
| 2015/0359755 A1 | 12/2015 | Guy et al. |
| 2016/0136114 A1 | 5/2016 | Ceulemens et al. |
| 2016/0228454 A1 | 8/2016 | Zhang et al. |
| 2016/0249863 A1 | 9/2016 | Ando |
| 2016/0279159 A1 | 9/2016 | Hirano et al. |
| 2017/0020885 A1 | 1/2017 | Hsu |
| 2017/0056344 A1 * | 3/2017 | Farr ................ A61K 31/137 |
| 2017/0071940 A1 | 3/2017 | Olaleye et al. |
| 2017/0071949 A1 | 3/2017 | De Witte et al. |
| 2017/0135594 A1 | 5/2017 | Hartings et al. |
| 2017/0151194 A1 | 6/2017 | Ceulemens |
| 2017/0151214 A1 | 6/2017 | Ceulemens et al. |
| 2017/0151257 A1 | 6/2017 | Ceulemens |
| 2017/0151259 A1 | 6/2017 | Ceulemens |
| 2017/0174613 A1 | 6/2017 | Londesbrough et al. |
| 2017/0174614 A1 | 6/2017 | Farr et al. |
| 2017/0348303 A1 | 12/2017 | Bosse |
| 2018/0028499 A1 | 2/2018 | Baraban et al. |
| 2018/0055789 A1 | 3/2018 | Farr |
| 2018/0092864 A1 | 4/2018 | Martin et al. |
| 2018/0141953 A1 | 5/2018 | Dax |
| 2018/0148403 A1 | 5/2018 | Londesbrough et al. |
| 2018/0215701 A1 | 8/2018 | Carroll et al. |
| 2018/0221319 A1 | 8/2018 | During |
| 2018/0271821 A1 | 9/2018 | Gold |
| 2018/0325909 A1 | 11/2018 | DeWitte |
| 2019/0083425 A1 | 3/2019 | Farr |
| 2019/0091173 A1 | 3/2019 | Farfel |
| 2019/0091174 A1 | 3/2019 | Galer |
| 2019/0091175 A1 | 3/2019 | Morrison |
| 2019/0091176 A1 | 3/2019 | Galer |
| 2019/0091177 A1 | 3/2019 | Galer |
| 2019/0091179 A1 | 3/2019 | Morrison |
| 2019/0125697 A1 | 5/2019 | Farfel |
| 2019/0247333 A1 | 8/2019 | Farfel |
| 2019/0308017 A1 | 10/2019 | Edgerton et al. |
| 2019/0380979 A1 | 12/2019 | Galer |
| 2020/0030260 A1 | 1/2020 | Sherrington et al. |
| 2020/0030341 A1 | 1/2020 | Ceulemens |
| 2020/0170965 A1 | 6/2020 | Boyd |
| 2020/0237683 A1 | 7/2020 | Whalley et al. |
| 2020/0261380 A1 | 8/2020 | Abu-Izza |
| 2020/0276136 A1 | 9/2020 | Galer |
| 2020/0297665 A1 | 9/2020 | Martin |
| 2020/0306210 A1 | 10/2020 | Morrison |
| 2020/0330406 A1 | 10/2020 | Galer |
| 2021/0113495 A1 | 4/2021 | Boyd |
| 2021/0121479 A1 | 4/2021 | Ceulemens |
| 2021/0147335 A1 | 5/2021 | Londesbrough |
| 2021/0158920 A1 | 5/2021 | Stewart et al. |
| 2021/0267916 A1 | 9/2021 | Farr |
| 2021/0299064 A1 | 9/2021 | Morrison |
| 2021/0330610 A1 | 10/2021 | Martin |
| 2021/0393550 A1 | 12/2021 | Farr |
| 2021/0401776 A1 | 12/2021 | Martin |
| 2022/0016053 A1 | 1/2022 | Galer |
| 2022/0096514 A1 | 3/2022 | Quan |
| 2022/0125743 A1 | 4/2022 | Farr |
| 2022/0133652 A1 | 5/2022 | Millet |
| 2022/0160727 A1 | 5/2022 | Ceulemens |
| 2022/0193082 A1 | 6/2022 | DeWitte et al. |
| 2022/0226262 A1 | 7/2022 | Boyd et al. |
| 2022/0289663 A1 | 9/2022 | Farr et al. |
| 2022/0370381 A1 | 11/2022 | Martin et al. |
| 2023/0076320 A1 | 3/2023 | Martin et al. |
| 2023/0078820 A1 | 3/2023 | Cha et al. |
| 2023/0165810 A1 | 6/2023 | Galer |

FOREIGN PATENT DOCUMENTS

| | | |
|---|---|---|
| CN | 103025301 | 4/2013 |
| CN | 103502245 A | 1/2014 |
| CN | 103886415 | 6/2014 |
| CN | 104800168 | 7/2015 |

(56) References Cited

FOREIGN PATENT DOCUMENTS

| | | |
|---|---|---|
| CN | 111971035 | 11/2020 |
| DE | 2150399 | 4/1973 |
| EP | 0 441 160 | 8/1991 |
| EP | 0 810 195 | 12/1997 |
| EP | 0 920 864 | 6/1999 |
| EP | 1 399 015 | 1/2010 |
| EP | 2 399 513 | 12/2011 |
| EP | 3170807 | 5/2017 |
| FR | 2663539 | 12/1991 |
| GB | 1413078 | 7/1973 |
| GB | 1399015 | 6/1975 |
| GB | 1413070 | 11/1975 |
| GB | 2531282 | 4/2016 |
| GB | 2568809 A * 5/2019 | ............ A61K 31/05 |
| HU | 204497 | 1/1992 |
| JP | A S64-066116 | 3/1989 |
| JP | H05-310564 A | 11/1993 |
| JP | A-2008-536545 | 9/2008 |
| JP | A-2009-525977 | 7/2009 |
| JP | A 2010-520162 | 6/2010 |
| JP | A-2011-221623 | 11/2011 |
| JP | A-2011-529923 | 12/2011 |
| JP | A-2012-511969 | 5/2012 |
| JP | A-2012-520130 | 9/2012 |
| JP | A-2012-208669 | 10/2012 |
| JP | A-2013-536857 | 9/2013 |
| JP | A-2013-248329 | 12/2013 |
| JP | 2016 216438 A | 12/2016 |
| RU | 2317104 | 2/2008 |
| RU | 103209 | 3/2011 |
| RU | 2503448 | 1/2014 |
| RU | 2571501 | 12/2015 |
| WO | WO 1994/018962 | 9/1994 |
| WO | WO 1995/04713 | 2/1995 |
| WO | WO 1995/32962 | 12/1995 |
| WO | WO 2001/86506 | 11/2001 |
| WO | WO 2003/026591 | 4/2003 |
| WO | WO 2003/077847 | 9/2003 |
| WO | WO 2005/004865 | 1/2005 |
| WO | WO 2006/034465 | 3/2006 |
| WO | WO 2006/100676 | 9/2006 |
| WO | WO 2007/034476 | 3/2007 |
| WO | WO 2007/073503 | 6/2007 |
| WO | WO 2007/079181 | 7/2007 |
| WO | WO 2007/092469 | 8/2007 |
| WO | WO 2008/025148 | 3/2008 |
| WO | WO 2008/104524 | 9/2008 |
| WO | WO 2009/087351 | 7/2009 |
| WO | WO 2010/015029 | 2/2010 |
| WO | WO 2010/020585 | 2/2010 |
| WO | WO 2010/025931 | 3/2010 |
| WO | WO 2010/075115 | 7/2010 |
| WO | WO 2010/104841 | 9/2010 |
| WO | WO 2010/121022 | 10/2010 |
| WO | WO 2011/112606 | 9/2011 |
| WO | WO 2011/146850 | 11/2011 |
| WO | WO 2012/030927 | 3/2012 |
| WO | WO 2012/093255 | 7/2012 |
| WO | WO 2012/154812 | 11/2012 |
| WO | WO 2013/096878 | 6/2013 |
| WO | WO 2013/112363 | 8/2013 |
| WO | WO 2013/122897 | 8/2013 |
| WO | WO 2014/177676 | 11/2014 |
| WO | WO 2015/013397 | 1/2015 |
| WO | WO 2015/026849 | 2/2015 |
| WO | WO 2015/066344 | 5/2015 |
| WO | WO 2015/163098 | 10/2015 |
| WO | WO 2015/193668 | 12/2015 |
| WO | WO 2016/051271 | 4/2016 |
| WO | WO 2016/059403 | 4/2016 |
| WO | WO 2016/138138 | 9/2016 |
| WO | WO 2016/205671 | 12/2016 |
| WO | WO 2017/035267 | 3/2017 |
| WO | WO 2017/112702 | 6/2017 |
| WO | WO 2017/122701 | 6/2017 |
| WO | WO 2017/170354 | 10/2017 |
| WO | WO 2018/037306 | 3/2018 |
| WO | WO 2018/060732 | 4/2018 |
| WO | WO 2018/206924 | 11/2018 |
| WO | WO 2019/064031 | 4/2019 |
| WO | WO 2019/067405 | 4/2019 |
| WO | WO 2019/067413 | 4/2019 |
| WO | WO 2019/067419 | 4/2019 |
| WO | WO-2019064031 A1 * 4/2019 | ............ A61K 31/05 |
| WO | WO 2019/204593 | 10/2019 |
| WO | WO 2019/216919 | 11/2019 |
| WO | WO 2019/241005 | 12/2019 |
| WO | WO 2020/014075 | 1/2020 |
| WO | WO 2020/105005 | 5/2020 |
| WO | WO 2020/112460 | 6/2020 |
| WO | WO 2020/176276 | 9/2020 |
| WO | WO 2021/156437 | 8/2021 |
| WO | WO 2022/013425 | 1/2022 |
| WO | WO 2022/069489 | 4/2022 |
| WO | WO 2023/034115 | 3/2023 |
| WO | WO 2023/101866 | 6/2023 |

OTHER PUBLICATIONS

Campbell, et al. (1971, Plasma concentrations of fenfluramine and its metabolite, norfenfluramine, after single and repeated oral administration, Br. J. Pharmacol., 43, 465-466 (Year: 1971).*
Nickels et al., (Apr. 2017), Stiripentol in the Management of Epilepsy, CNS Drugs, 31, 405-416 (Year: 2017).*
Zhang et al., 2016, A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS) (poster), American Conference on Pharmacometrics (Year: 2016).*
Devinsky et al. (2021, Effect of Fenfluramine on convulsive seizures in CDKL5 deficiency disorder, Epilepsia, 62, e98-e102 (Year: 2021).*
Asatryan, Babken "Challenges in Decoding Sudden Unexpected Death in Epilepsy: The Intersection Between Heart and Brain in Epilepsy" Journal of the American Heart Association (2021) 10(23):e023571, pp. 1-4.
BNF 39—British National Formulary (Mar. 2000) p. 197.
Caraballo et al., "Ketogenic diet in patients with Lennox-Gastaut syndrome" Seizure (2014) 23:751-755.
Cross et al., "Expert Opinion on the Management of Lennox-Gastaut Syndrome: Treatment Algorithms and Practical Considerations" Frontiers in Neurology (Sep. 29, 2017) 8(505):1-18.
Fisher et al., "Definition of the postictal state: When does it start and End?" Epilepsy & Behavior (2010) 19(2):100-104.
Grosso et al., "Dexfenfluramine effective in drug-resistant temporal lobe epilepsy" Neurology, Lippincott Williams & Wilkins, Philadelphia, US (Sep. 25, 2001) 57(6):1139-1140.
Hay et al., "Clinical development success rates for investigational drugs" Nature Biotechnology (Jan. 2014) 32(1):40-51.
Knupp et al., "Efficacy and Safety of Fenfluramine for the Treatment of Seizures Associated with Lennox-Gastaut Syndrome" JAMA Neurology (Jun. 2022) 79(6):554-564.
MIMS—Monthly Index of Medical Specialties (Sep. 1997) pp. 240-241.
Samanta, Debopam "Changing Landscape of Dravet Syndrome Management: An Overview" Neuropediatrics (2020) 51(2):135-145.
Archer et al., "Primary Pulmonary Hypertension, A Vascular Biology and Translational Research "Work in Progress"" Clinical Cardiology: New Frontiers, Circulation, 102:2781-2791 (Nov. 28, 2000).
Echocardiogram, Echocardiogram Test for Pulmonary Arterial Hypertension PAH (https://pulmonaryhypertensionm.com/echocardiogram/) pp. 1-5 (Jan. 4, 2012).
FDA—approved Treatments for Pulmonary Hypertension, Vera Moulton Wall Center for Pulmonary Vascular Diseases, Stanford (https://med.stanford.edu/wallcenter/patient-resources/fda.html) pp. 1-8 (Jan. 19, 2017).

(56) References Cited

OTHER PUBLICATIONS

Gardner, Amanda "Living Your Best With Pulmonary Hypertension" WebMD, pp. 1-5 (Jan. 2, 2019).
Khan et al., "Epileptic Encephalopathies: An Overview" Epilepsy Research and Treatment, vol. 2012, pp. 1-8 (Sep. 12, 2012).
Mari et al., "CDKL5 belongs to the same molecular pathway of MeCP2 and it is responsible for the early-onset seizure variant of Rett syndrome" Human Molecular Genetics (2005) 14(14):1935-1946.
Pulmonary Hypertension and Edema, (pulmonaryhypertensionnews.com/pulmonary-hypertension-and-edema/) pp. 1-3 (Nov. 9, 2015).
Scheffer et al., "ILAE classification of the epilepsies: Position paper of the ILAE Commission for Classification and Terminology" Epilepsia (2017) 58)4):512-521.
Specchio et al., "International League Against Epilepsy classification and definition of epilepsy syndromes with onset in childhood: Position paper by the ILAE Task Force on Nosology and Definitions" Epilepsia (Mar. 17, 2022) 00:1-45.
Weir et al., "Anorexic Agents Aminorex, Fenfluramine, and Dexfenfluramine Inhibit Potassium Current in Rat Pulmonary Vascular Smooth Muscle and Cause Pulmonary Vasoconstriction" American Heart Association, Circulation, 94(9):2216-2220 (Nov. 1996).
Zuberi et al., "Commentary: A New Classification is Born" International League Against Epilepsy (2017) pp. 511.
Devane et al., "Dosage Regimen Design" Pharmacology & Therapeutics (1982) 17(2):143-163.
Dominguez-Gonzalez et al., "Deoxynucleoside Therapy for Thymidine Kinase 2-Deficient Myopathy" Annals of Neurology (2019) 86(2):293-303.
ONFI Prescribing Information. Lundbeck, Deerfield, Reference ID: 4028780 [online], Dec. 2016, [retrieved on Jun. 22, 2021, <URL: https://www.accessdata.fda.gov/drugsatfda_docs/label/2016/203993s005lbl.pdf>.
Study NCT02926898 on Date: May 1, 2017 (v6), ClinicalTrials.gov archive[online], May 1, 2017, [retrieved on Jun. 22, 2021], <URL: https://clinicaltrials.gov/ct2/history/NCT02926898>.
Zaccara et al., "Interactions between antiepileptic drugs, and between antiepileptic drugs and other drugs" Seminar in Epileptology (2014) 16(4):409-432.
Anandam, R., Affiliations Indian Journal of Pediatrics (Jan. 1, 2000) 67 (1 Suppl):S88-91 (Abstract Only).
Anonymous, "Determination That PONDIMIN (Fenfluramine Hydrochloride) Tablets, 20 Milligrams and 60 Milligrams, and PONDEREX (Fenfluramine Hydrochloride) Capsules, 20 Milligrams Were Withdrawn From Sale for Reasons of Safety or Effectiveness", Federal Register, (Sep. 29, 2015).
Anonymous, "MacReportMedia—Brabant Pharma Reports Two-Year Follow-up Data From a 19-year Observational Study Using Low-Dose Fenfluramine for the Treatment of Dravet Syndrome", Nov. 25, 2013 (Nov. 25, 2013).
Anonymous "Selective Serotonin reuptake Inhibitor—Wikipedia" Internet https://en.wikipedia.org/wiki/Selective_serotonin_reuptake_inhibitor (Feb. 1, 2020 (retrived on Feb. 4, 2020)).
Aras et al., "The European patient with Dravet Syndrome: Results from a parent-reported survey on antiepileptic drug use in the European population with Dravet Syndrome" Epilepsy & Behavior (2015) 44:104-109.
Arzimanoglou, "Dravet syndrome: From electroclinical characteristics to molecular biology" Epilepsia, 50(Suppl. 8):3-9 (2009).
Boel and Casaer, "Add-on Therapy of Fenfluramine in Intractable Self-Induced Epilepsy" Neuropaediatrics 1996, 27(4):171-173.
F Brenot et al., "Primary Pulmonary Hypertension and Fenfluramine Use.", Heart, vol. 70, No. 6, Dec. 1, 1993 (Dec. 1, 1993), pp. 537-541.
Brunklaus et al., "Prognostic, clinical and demographic features in SCN1A mutation-positive Dravet syndrome" Brain, 2012, p. 1-8.
Brunklaus et al., "Dravet syndrome—From epileptic encephalopathy to channelopathy" Epilepsia (May 16, 2014) 55(7):979-984.

Buchanan, Gordon F. et al., Serotonin neurones have anticonvulsant effects and reduce seizure-induced mortality, The Journal of Physiology, 2014, vol. 592, Issue 19, p. 4395-4410.
Carvalho et al., "d-Amphetamine Interaction with Glutathione in Freshly Isolated Rat Hepatocytes" Chemical Research in Toxicology (Jan. 1996) 9(6):1031-1036.
Casaer et al., "Fenfluramine as a Potential Antiepileptic Drug" Epilepsia, 43(2), 205-206, 2002.
C. B. Catarino et al. "Dravet Syndrome as epileptic encephalopathy: Evidence from long-term course and neuropathology", Brain, vol. 134, No. 10 (Jun. 29, 2011) pp. 2982-3010.
Ceulemans et al., "Poster presented at the 69$^{th}$ Annual Meeting of the American Epilepsy Society" (Dec. 2015) Philadelphia.
Ceulemans et al., "Successful use of fenfluramine as an add-on treatment for Dravet syndrome" Epilepsia, 53(7), 2012, 1131-1139.
Ceulemans, "Overall management of patients with Dravet syndrome" Developmental Medicine & Child Neurology, 2011, 53, 19-23.
Ceulemans B et al., "Successful use of Fenflurarmine as add-on treatment in Dravet syndrome: a two year prospective follow up", European Journal of Paediatric Neurology, vol. 17, 01101866, Sep. 1, 2013 (Sep. 1, 2013).
Ceulemans B., "Successful Use of Fenfluramine as Add-On Treatment in Dravet Syndrome" Epilepsia, 52(Suppl. 6):4-22 (2011).
Ceulemans et al., "Five-year extended follow-up status of 10 patients with Dravet syndrome treated with fenfluramine" Epilepsia (May 20, 2016) 57(7):e129-e134.
Chiron et al., "The pharmacologic treatment of Dravet syndrome" Epilepsia (2011) 52(Suppl 2):72-75.
Clemens B., "Dopamine agonist treatment of self-induced pattern-sensitive epilepsy. A case Report" Epilepsy Res. 2. 1988, p. 340-343.
Clinical Trials ClinicalTrials.gov Identifier: NCT02224560 (Jul. 27, 2018).
Curzon et al., "Appetite suppression by commonly used drugs depends on 5-HT receptors but not on 5-HT availability" Tips (1997) 18:21-25.
Devinsky et al., "Trial of Cannabidiol for Drug-Resistant Seizures in the Dravet Syndrome" The New Engalnd Journal of Medicine (May 25, 2017) 376(21):2011-2020.
C. Doege et al., "Myoclonic-astatic epilepsy: Doose-Syndrum 2014: Doose syndrome 2014", Zeitschrift FR Epileptologie, (Mar. 20, 2014).
Döring et al. "Thirty Years of Orphan Drug Legislation and the Development of Drugs to Treat Rare Seizure Conditions: A Cross Sectional Analysis" PLOS One, pp. 1-15 (Aug. 24, 2016).
Dravet, Charlotte, "The core Dravet syndrome phenotype" Epilepsia, 52(Supp. 2):3-9 (2011).
Faingold et al., "Prevention of seizure-induced sudden death in a chronic SUDEP model by semichronic administration of a selective serotonin reuptake inhibitor" Epilepsy & Behavior (2011) 22:186-190.
Favale et al., "The anticonvulsant effect of citalopram as indirect evidence of serotonergic impairment in human epileptogenesis" Seizure (2003) 12:316-319.
Franco-Perez, Javier "The Selective Serotonin Reuptake Inhibitors: Antidepressants with Anticonvulsant Effects?" Ann Deoress Anxiety (2014) 1(5):1025 (2 pages).
Gastaut et al., "Compulsive respiratory sterotypies in children with autistic features: Polygraphic recording and treatment with fenfluramine" Journal of Autism and Developmental Disorders, (Sep. 1, 1987) 17(3):391-406.
K Gentsch et al., "Laboratory Research Fenfluramine Blocks Low-Mg2'-Induced Epileptiform Activity in Rat Entorhinal Cortex" Epilepsia, Jan. 1, 2000 (Jan. 1, 2000), pp. 925-928.
Gharedaghi et al., "The role of different serotonin receptor subtypes in seizure susceptibility" Exp. Brain Res (2014) 232:347-367.
Gioia et al., "Confirmatory Factor Analysis of the Behavior Rating Inventory of Executive Function (BRIEF) in a Clinical Sample" Child Neuropsychology (2002) 8(4):249-57.
Habibi et al., "The Impact of Psychoactive Drugs on Seizures and Antiepileptic Drugs" Current Neurology and Neuroscience Reports (Jun. 17, 2016) 16(8):1-10.

(56) References Cited

OTHER PUBLICATIONS

Haritos et al., "Metabolism of dexfenfluramine in human liver microsomes and by recombinant enzymes: Role of CYP2D6 and 1A2" Pharmcogenetics (Oct. 1998) 8(5):423-432.
Harvard Health Publishing, Harvard Medical School Generalized Seizures (Grand Mal Seizures) (Apr. 2014) pp. 1-5 (https://www.health.hearvard.edu/diseases-and-conditions/generalized-seizures-grand-mal-se . . . ).
Hazai et al., "Reduction of toxic metabolite formation of acetaminophen" Biochemical and Biophysical Research Communications (Mar. 8, 2002) 291(4):1089-1094.
Hegadoren et al., "Interactions of iprindole with fenfluramine metabolism in rat brain and liver" Journal of Psychiatry & Neuroscience (Mar. 1991) pp. 5-11.
Inoue et al., "Stiripentol open study in Japanese patients with Dravet Syndrome" Epilepsia, 50(11):2362-2368 (2009).
Isaac, Methvin, Serotonergic 5-HT2C Receptors as a Potential Therapeutic Target for the Design Antiepileptic Drugs, Current Topics in Medicinal Chemistry, 2005, vol. 5, Issue 1, p. 59-67.
Katholieke Universiteit Leuven, University Hospital Antwerp: "Interim results of a fenfluramine open-label extension study", European Patent Register (May 25, 2017).
Klein et al., "Cannabidiol potentiates Delta$^9$-tetrahydrocannabinol (THC) behavioural effects and alters THC pharmacokinetics during acute and chronic treatment in adolescent rats" Psychopharmacology (2011) 218:443-457.
Klein, M. T. and Teitler, M. , Distribution of 5-htlE receptors in the mammalian brain and cerebral vasculature: an immunohistochemical and pharmacological study, British Journal of Pharmacology, Jun. 2012, vol. 166, No. 4, p. 1290-1302.
Lagae et al. "A pilot, open-label study of the effectiveness and tolerability of low-dose ZX008 (fenfluramine HC1) in Lennox-Gastaut syndrome" Epilepsia (2018) 59: 1881-1888.
Leit, Silvana et al., Design and synthesis of tryptamine-based 5HT2C agonists for the treatment of certain CNS disorders, Division of Medicinal Chemistry Scientific Abstracts for the 240th National ACS Meeting and Exposition, Jul. 28, 2010, MEDI367.
LeJeune et al., "Psychometric Support for an Abbreviated Version of the Behavior Rating Inventory of Executive Function (BRIEF) Parent Form" Child Neuropsychology (2010 16:182-201.
Lopez-Meraz et al., "5-HT$_{1A}$ receptor agonist modify epileptic seizures in three experimental models in rats" Neuropharmacology (2005) 49:367-375.
Manzke et al., "5-HT4(a) receptors avert opiod-induced breathing depression without loss of analgesia" Science (Jul. 11, 2003) 301:226-229.
Martin, et al., "An Examination of the Mechanism of Action of Fenfluramine in Dravet Syndrome: A Look Beyond Serotonin" Presented as part of the Zogenix Scientific Exhibit During the 70$^{th}$ Annual Meeting of the American Epilepsy Society, Houston, Texas (Dec. 2-6, 2016).
Meador K J., "Seizure reduction with fluoxetin in an adult woman with Dravet syndrome", Epilepsy & Behavior Case Reports, Elsevier BV, NL, vol. 2, Jan. 1, 2014 (Jan. 1, 2014), pp. 54-56.
Mudigoudar et al., "Emerging Antiepileptic Drugs for Severe Pediatric Epilepsies" Seminars in Pediatric Neurology (Jun. 2016) 23(2):167-179.
Mulley et al., "SCN1A Mutations and Epilepsy" Human Mutation (2005) 25:535-542.
Naithani et al., "The Conventional Antiepileptic Drug Use When Compared to a Combination Therapy Regime in a Teaching Hospital in India" International Journal of Pharma and Bio Sciences (2012) 3(1):B-191-B-197.
NCT02682927 (Sep. 3, 2016, 10 pages) Accessed from https://www.clinicaltrials.gov/ct2/history/NCT02682927?V_=View#StudyPageTop on Mar. 18, 2019).
Nozulak et al., "(+)-cis-4,5,7a,8,9, 10, 11, 11a-Octahydro-7H-10-methylindolo[1,7-bc][2,6]-naphthridine: A 5-HT$_{2C/2B}$ Receptor Antagonist with Low 5-HT2A Receptor Affinity" J. Med. Chem. (1995) 38:28-33.

Olson et al., "Cyclin-Dependent Kinase-Like 5 Deficiency Disorder: Clinical Review" Pediatric Neurology (2019) 97:18-25.
O'Neill et al., "GR46611 potentiates 5-HT$_{1A}$ receptor-mediated locomotor activity in the guinea pig" European Journal of Pharmacology (1999) 370:85-92.
Pirincci et al., "The Effects of Fefluramine on Blood and Tissue Seratonin (5-Hydroxytryptamine) Levels in Rats" Turk J Vet Anim Sci (2005) 29:857-863.
Pittala, Valeria et al., 5-HT7 Receptor Ligands: Recent Developments and Potential Therapeutic Applications, Mini-Reviews in Medicinal Chemistry, 2007, vol. 7, Issue 9, p. 945-960.
Jake Remaly: "Fenfluramine Reduces Convulsive Seizure Frequency in Dravet Syndrome. Epilepsy Resource Center", Jan. 1, 2018 (Jan. 1, 2018).
Remington, "The Science and Practice of Pharmacy", Nineteenth Edition (1995), pp. 710-712.
Rho, Jong M. "Basic Science Behind the Catastrophic Epilepsies" Epilepsia (2004) 45(Suppl. 5):5-11.
Rothman et al., "Serotonergic drugs and valvular heart disease" Expert Opinion on Drug Safety (May 2009) 8(3):317-329.
Russo et al., "Agonistic Properties of Cannabidiol at 5-HT1a Receptors" Neurochemical Research (2005) 30(8):1037-1043.
Scala et al., "CDKL5/STK9 is mutated in Rett syndrome variant with infantile spasms" J Med Genet (2005) 42:103-107.
Schoonjans, An-Sofie "Low-dose fenfluramine in the treatment of neurologic disorders: experience in Dravet syndrome" Therapeutic Advances in Neurological Disorders (Jan. 1, 2015) pp. 328-338.
Schoonjans et al. "Low-dose fenfluramine significantly reduces seizure frequency in Dravet syndrome: a prospective study of a new cohort of patients", European Journal of Neurology, vol. 24, No. 2, (Oct. 28, 2016), pp. 309-314.
An-Sofie Schoonjans et al: "Cardiovascular Safety of Low-Dose Fenfluramine in Dravet Syndrome: A Review of its Benefit-Risk Profile in a New Patient Population", Current Medical Research and Opinion, vol. 33, No. 10, Jul. 31, 2017 (Jul. 31, 2017), pp. 1773-1781.
Selmer et al., "SCN1A mutation screening in adult patients with Lenox-Gastaut syndrome features" Epilepsy & Behavior (Nov. 1, 2009) 16(3):555-57.
Sharma et al. Indian Journal of Pharmacology, 1996, 28(1), 1-10.
Slick et al., "Frequency of Scale Elevations and Factor Structure of the Behavior Rating Inventory of Executive Function (Brief) in Children and Adolescents with Intractable Epilepsy" Child Neuropsychology (2006) 12:181-189.
Sourbron et al., "Serotonergic Modulation as Effective Treatment for Dravet Syndrome in Zebrafish Mutant Model" ACS Chemical Neuroscience (Feb. 17, 2016) 7(5):588-598.
Sullivan et al. "Effext of ZX008 (fenfluramine HC1 oral solution) on total seizures in Dravet syndrome" Neurology: Official Journal of the American Academy of Neurology, 2018, 90(24):e2187-e2811.
Van Rijckevorsel, Kenou, "Treatment of Lennox-Gastaut syndrome: overview and recent findings" Neuropsychiatric Disease and Treatment, 4(6):1001-1019 (2008).
Vickers et al., "Oral Administration of the 5-HT2C receptor agonist, mCPP, reduces body weight gain in rats over 28 days as a result of maintained hypophagia" Psychopharmacology (May 2003), 167 (3): 274-280.
Viola et al., "The Behavior Rating Inventory of Executive Function (BRIEF) to Identify Pediatric Acute Lymphoblastic Leukemia (ALL) Survivors At Risk for Neurocognitive Impairment" Journal of Pediatric Hematology/Oncology (Apr. 1, 2017) 39(3):174-178.
Wallace et al., "Pharmacotherapy for Dravet Syndrome" Paediatr. Drugs, 18(3):197-208 (Jun. 2016).
Wirrell et al., "Stiripentol in Dravet syndrome: Results of a retrospective U.S. study" Epilepsia (2013) 54(9):1595-1604.
Wirrell et al., "Stiripentol in Dravet syndrome: Is it Worth It?" Epilepsy Currents, 14(1):22-23 (Jan./Feb. 2014).
Wirrell et al., "Treatment of Dravet Syndrome" Can. J. Neurol. Sci., 43(Suppl. 3):S13-18 (Jun. 2016).
Wirrell et al., "Optimizing the Diagnosis and Management of Dravet Syndrome: Recommendations From a North American Consensus Panel" Pediatric Neurology (Mar. 2017) 68:18-34.

(56) References Cited

OTHER PUBLICATIONS

Wurtman et al., "Fenfluramine and other serotoninergic drugs depress food intake and carbohydrate consumption while sparing protein consumption" Current Medical Research and Opinion (1979) 6(1 Supp):28-33.

Yamaori et al., "Potent inhibition of human cytochrome P450 3A isoforms by cannabidiol: Role of phenolic hydroxyl groups in the resorcinol moiety" Life Sciences (2011) 88:730-736.

Yoshida et al. (2017), "Impact of Physiologically Based Pharmacokinetic Models on Regulatory Reviews and Product Labels: Frequent Utilization in the Field of Oncology" in Clinical Pharmacology and Therapeutics 2017; 101(5): 597-602.

Zhang et al., *A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS)*. Presented at the 2016 American Conference for Pharmacokinetics.

Zhang et al., A Physiological-based Pharmacokinetic (PBPK) Modeling Approach to Quantifying Drug-Drug Interactions: Applications to the Development of Fenfluramine (ZX008) for Treatment of Seizures in Dravet Syndrome (DS). Published in Abstracts accepted for American Conference on Pharmacometrics 2016 (ACoP7).

Zhang et al., "Pharmacological Characterization of an Antisense Knockdown Zebrafish Model of Dravet Syndrome: Inhibition of Epileptic Seizures by the Serotonin Agonist Fenfluramine" Plos One (May 12, 2015) 10(5)::16-17 (Abstract).

Zhuang et al. (2016), "PBPK modeling and simulation in drug research and development" in Acta Pharmaceutica Sinica B 2016;6(5):430-440.

ZOGENIX "Corporate Update Nasdaq: ZGNX" (Jun. 1, 2016) Retrieved from the Internet: URL:http://www.jefferies.com/CMSFiles/Jefferies.com/files/Conferences/060716/Present tions/Zogenix%20Inc.pdf [retrieved on Feb. 21, 2018].

Anonymous, "Health Technology Briefing: Fenfluramine hydrochloride for treatment of seizures associated with Lennox-Gastaut syndrome" NIHR Innovation Observatory (May 2019) 8 pages.

Anonymous "Zogenix Announces Positive Top-Line Results from Global Pivotal Phase 3 Trial of FINTEPLA for the treatment of Lennox-Gastaut Syndrome" Bio Space (Feb. 6, 2020) pp. 1-12.

Baker, M. "Zogenix Completes Enrollment in Phase 3 Trial of FINTEPLA in Lennox-Gastaut Syndrome" (Jul. 8, 2019) 2 pages.

Kelley et al., "Doose syndrome (myoclonic-astatic epilepsy): 40 years of progress" Developmental Medicine & Child Neurology (2010) 52(11):988-993.

McTague et al., "The genetic landscape of the epileptic encephalopathies of infancy and childhood" Lancet Neurol. (2016) 15:304-316.

Ohuni et al., "Treatment and Long-Term Prognosis of Myoclonic-Astatic Epilepsy of Early Childhood ," Neuropediatrics (2002) 33(3):122-32.

ZOGENIX "Corporate Update Nasdaq: ZGNX" (Jun. 1, 2016) Retrieved from the Internet: URL:http://www.jefferies.com/CMSFiles/Jefferies.com/files/Conferences/060716/Presentations/Zogenix%20Inc.pdf [retrieved on Feb. 21, 2018].

Bagdy et al., "Serotonin and epilepsy," J. Neurochem., 100:857-73 (2007).

Ceulemans et al., "Clinical Correlations of Mutations in the SCN1A Gene: From Febrile Seizures to Severe Myoclonic Epilepsy in Infancy" Pediatr. Neurol. 30(4):236-43 (2004).

Coleman et al., "Monitoring for adverse drug reactions," Br. J. Clin. Pharmacol., 61(4):371-78 (2006).

"Diacomit: EPAR—Scientific Discussion," European Medicines Agency ("EPAR Diacomit") https://www/ema/europa.eu/en/documents/scientific-discussion/diacomit-epar-scientific-discussion on.pdf, published 2009.

Ferretti et al., "Direct High-performance liquid chromatograph resolution on a chiral col. of dexfenfluramine and its impurities, in bulk raw drug and pharmaceutical formulations" J. Chromatogr. A. 731:340-45 (1996).

Gordon et al., "A SARS-COV-2 protection interaction map reveals targets for drug repurposing" Nature (Apr. 30, 2020) 583(7816:459-468.

Haute Autorité de Santé (HAS), French National Authority for Health, issued an opinion on Diacomit ("HAS Opinion") https://www.has-sante.fr/upload/dox/application/pdf/2010-01/diacomit_ct_4347.pdf (Jun. 6, 2007).

Heisler et al., "Epilepsy and Obesity in Serotonin 5-HT$_{2c}$ Receptor Mutant Mice," Ann. NY Acad. Sci. 861:74-78 (1998).

International Conference on Harmonisation of Technical Requirements for Registration of Pharmaceuticals for Human Use, "ICH Harmonised Tripartite Guidline: Impurities in New Drug Substances," Q3A(R2) (2006).

Jingyu et al., "Study on Synthesis of Amphetamine Compounds" Chem J. of Chinese Univ., 9(2), 12 pages (1988).

Martin et al., "Fenfluramine acts as a positive modulator of sigma-1 receptors" Epilepsy and Behavior, Academic Press, San Diego, CA, US (Mar. 10, 2020) 105:1-9.

Mathews et al., "Effect of D-Fenfluramine on the Lymphocyte Response of HIV+ Humans" International Journal of Immunopharmacology (Jan. 1, 1998) 20:751-763.

Public Law 110-85, 110th Congress ("FDA Amendments Act of 2007") published 2007.

Rothman et al., "(+)-Fenfluramine and Its Major Metabolite, (+)-Norfenfluramine, Are Potent Substrates for Norepinephrine Transporters," J. Pharmacol. Exp. Ther., 305(3):1191-99 (2003).

Tran et al., "Dakin-West Synthesis of β-Aryl Ketones" J. Org. Chem. (2006) 71:6640-6643.

Vela, Jose Miguel "Repurposing Sigma-1 Receptor Ligands for COVID-19 Therapy?" Frontiers in Pharmacology (Nov. 9, 2020) 11:1-23.

Wee et al., "Risk for Valvular Heart Disease among Users of Fenfluramine and Dexfenfluramine Who Underwent Echocardiography before Use of Medication," Annals of Internal Medicine, 129(11):870-874 (1998).

Aicardi et al., "Treatment of Self-Induced Photosensitive Epilepsy with Fenfluramine" New England Journal of Medicine (1985) 313:1419.

Aicardi et al., "Syncopal Attacks Compulsively Self-induced by Valsalva's Maneuver Associated with Typical Absence Seizures" Archives of Neurology (1988) 45:923-925.

Bird et al., "Combination of pharmaceutical compositions for treatment of neurological disorders" STN International (Columbus, Ohio) HCAPLUS database, Accession No. 2013:83254 (2013).

Coma et al., "New combination therapies for treating neurological dissorders" STN International (Columbus, Ohio) HCAPLUS database, Accession No. 2013:682383 (2013).

Cozzi et al., "Indan Analogs of Fenfluramine and Norfenfluramine Have Reduced Neurtoxic Potential" Pharmacology Biochemistry and Behavior (1998) 59(3):709-715.

Dimpfel et al., "Hesperidin and hesperetin for the treatment of epilepsy migraine, schizophrenia, depression, and drug abuse" STN International (Columbus, Ohio) HCAPLUS database, Accession No. 2006:1205690 (2006).

Droogmans et al., "Role of echocardiography in tox heart vavulopathy" European Journal of Echocardiography, 10:467-476 (2009).

Experimental Chemistry (Continued), Part 2, Separation and Purification, (Maruzen, Co., Ltd.), Jan. 25, 1967, pp. 159-162 and 184-193.

File History of U.S. Pat. No. 9,549,909 issued on Jan. 24, 2018 (571 pp).

File History of U.S. Pat. No. 9,603,815 issued on Mar. 28, 2017 (385 pp).

File History of U.S. Pat. No. 9,603,814 issued on Mar. 28, 2017 (466 pp).

File History of U.S. Pat. No. 9,610,260 issued on Apr. 4, 2017 (371 pp).

File History of U.S. Pat. No. 10,478,441 issued on Nov. 19, 2019 (761 pp).

File History of U.S. Pat. No. 10,478,442 issued on Nov. 19, 2019 (980 pp).

File History of U.S. Appl. No. 14/447,369, filed Jul. 30, 2014 (now abandoned) (285 pp.).

(56) References Cited

OTHER PUBLICATIONS

File History of U.S. Appl. No. 15/429,650, filed Feb. 10, 2017 (now abandoned) (267 pp).
File History of U.S. Appl. No. 15/429,641, filed Feb. 10, 2017 (now abandoned) (285 pp).
File History of U.S. Appl. No. 15/429,506, filed Feb. 10, 2017 (now abandoned) (641 pp).
File History of U.S. Appl. No. 16/596,166, filed Oct. 8, 2019 (now abandoned) (123 pp).
File History of U.S. Appl. No. 16/869,284, filed May 7, 2020 (now abandoned) (42 pp).
File History of U.S. Appl. No. 16/909,055, filed Jun. 12, 2020 (pending) (85 pp).
File History of U.S. Pat. No. 10,351,509 issued Jul. 16, 2019 (226 pp).
File History of U.S. Pat. No. 10,351,510 issued Jul. 16, 2019 (244 pp).
File History of U.S. Pat. No. 10,947,183 issued Mar. 16, 2021 (293 pp).
Garone et al., "Deoxypyrimidine monophosphate bypass therapy for thymidine kinase 2 deficiency" EMBO Molecular Medicine Aug. 1, 2014) 6(8):1016-1027.
Gross et al., "The influence of the sparteine/debrisoquine genetic polymorphism on the disposition of dexfenfluramine" Br J Clin Pharmacol (1996) 41:311-317.
Hattori et al., "A Screening test for the prediction of Dravet Syndrome before one year of age" Epilepsia (Apr. 2008) 49(4):626-633.
Hawkins et al., "Synthesis of [14C] Fenfluramine and [14C]-S780" Journal of Labelled Compounds (1974) 10(4):63-670.
Hirayama, Noriaki, Organic Compound Crystallization Handbook: Principles and Know-How (Maruzen, Co., Ltd.), Jul. 25, 2008, pp. 57-84.
Ji et al., "Study of Fenfluramine Synthesis Route" Journal of Shenyang College of Pharmacy (Apr. 1994) 11(2):116-118.
Kaiser et al., "Synthesis and Anorectic Activity o Some 1-Benzylcyclopropylamines" Journal of Medicinal Chemistry, American Chemical Society, US (1970) 13(5):820-826.
Lambert et al., "Inductive Enhancement of Aryl Participation" Journal of the American Chemical Society (Apr. 27, 1977) 99(9):3059-67.
Lewis et al., "Biosynthesis of Canescin, a Metabolite of *Aspergillus malignus*: Incorporation of Methionine, Acetate, Succinate, and Isocoumarin Precursors, Labelled with Deuterium and Carbon-13" J. Chem. Soc. Perkin Trans I (1988) pp. 747-754.
LoPinto-Khoury et al., "Antiepileptic Drugs and Markers of Vascular Risk" Curr Treat Options Neurol (Jul. 2010) 12(4):300-308.
Notification issued by the Director of Pharmaceutical and Medical Safety Bureau, Ministry of Health and Welfare, Guidelines for Residual Solvents in Pharmaceuticals, PMSB/ELD Notification No. 307, 1998, pp. 1-11.
Patani et al;, "Bioisosterism: A Rational Approach to Drug Design" Chem. Rev. (1996) 96:3147-3176.
Porra et al., "Determination of Fenfluramine Enantiomers in Pharmaceutical Formulations by Capillary Zone Electrophoresis" Chromatographia (Oct. 1995) 41(7/8):383-388.
Pottkamper et al., "The postictal state—What do we know?" Epilepsia (2020) 61(6):1045-1061.
Registry(STN) [online], Jun. 7, 2015, [Retrieval Date: Sep. 28, 2020], CAS Registry No. 1775169-27-1.
Remi et al., "Clinical features of the postictal state: Correlation with seizure variables" Epilepsy & Behavior (2010) 91(2):114-117.
Su et al., "The Synthesis of 2-Amino-1-Penylpropanes" Chemical Journal of Chinese Universities (1988) 9(2):134-139.
Subota et al., "Signs and Symptoms of the postictal period in epilepsy: A systematic review and meta-analysis" Epilepsy & Behavior (2019) 94:243-251.
Thurman et al., "Sudden expected death in epilepsy: Assessing the public health burden" Epilepsia (2014) 55(10):1479-1485.

Tupal et al., "Serotonin 5-HT$_4$ receptors play a critical role in the action of fenfluramine to block seizure-induced sudden death in a mouse model of SUDEP," Epilepsy Research (2021) 177:1-7.
Van Der Steldt et al., "The Effect of Alkyl Substitution in Drugs" Arzneimittelforschung—Drug Research (1965) 15:1251-1253.
Vivero et al., "A close look at fenfluramine and dexfenfluramine" The Journal of Emergency Medicine (1998) 16(2):197-205.
Werbel et al., "Synthesis, Antimalarial Activity, and Quantitative Structure-Activity Relationships of Tebuquine and a Series of Related 5-[(7-Chloro-4-quinolinyl)amino]-3[(alkylamino) methyl][1,1'-biphenyl]-2-ols and N omega-Oxides" J. Med. Chem. (1986) 29:924-939.
Anderson et al., "Spreading Depression: Imaging and Blockade in the Rat Neocortical Brain Slice," Journal of Neurophysiology 88(5):2713-3725 (Nov. 1, 2002).
Chiron, "Stiripentol for the treatment of Dravet syndrome" Orphan Drugs: Research and Reviews (2014) 4:29-38.
Ning et al., "Fenfluramine Directly Inhibits Cortical Spreading Depolarization—A Pathophysiologic Process Linked to SUDEP," American Epilepsy Society, pp. 1-3 (Nov. 11, 2021).
Bishop et al., "Fenfluramine treatment is associated with improvement in everyday executive function in preschool-aged children (<5 years) with Dravet syndrome: A critical period for early neurodevelopment," Epilepsy & Behavior (2023) 138:108994.
Brandt et I., "Cognitive adverse events of topiramate in patients with epilepsy and intellectual disability" Epilepsy & Behavior (2015) 45:261-264.
Chiron, "Stiripentol," Expert Opinion of Investigational Drugs, Informa Healthcare, UK (Jul. 1, 2005) 14(7):904-911.
Devinsky et al., "Sudden expected death in epilepsy: epidemiology, mechanisms and prevention," The Lancet Neurology, (2016) 15(10):1075-1088.
Park et al., "Long-Term cognitive and mood effects of zonisamide monotherapy in epilepsy patients" Epilepsy & Behavior (2008) 12:102-108.
Schoonjans et al. "fenfluramine significantly reduces seizure frequency in Dravet syndrome: a prospective study of a new cohort of patients", European Journal of Neurology, (Sep. 11, 2016), p. 1-1.
Strzelczyk et al., "Psychobehavioural and Cognitive Adverse Events of Anti-Seizure Medications for the Treatment of Developmental and Epileptic Encephalopathies" CNS Drugs (2002) pp. 1-33.
Aylward et al., "Screening and Assessment Tools" Developmental-Behavioral Pediatrics Evidence and Practice (2008) 123-201.
Berge et al., "Pharmaceutical Salts" J. Pharm Sci (1977) 68(1):1-19.
Busner et al., "Global Impressions Scale: Applying a Research Tool in Clinical Practice" Psychiatry (2007) 29-37.
Ceulemans B., "Successful Use of Fenfluramine as Add-On Treatment in Dravet Syndrome" Epilepsia, 52(Suppl. 6):4-22 (2011) (Abstract Only).
De Jonghe et al., "Molecular genetics of Dravet syndrome" Developmental Medicine & Child Neurology (2011) 53 (Supp 2):7-10.
Dravet. Charlotte, "Dravet Syndrome History" Developmental Medicine & Child Neurology (2011) 53 (Suppl. 2):1-6.
"Guideline on clinical investigation of medicinal products in the treatment of epileptic disorders" European Medicines Agency (Jul. 22, 2010) pp. 1-17.
Marini et al., "The genetics of Dravet Syndrome" Epilepsia (2011) 52(Suppl. 2):24-29.
Mayer et al., "Refractory Status Epilepticus" Archives of Neurology, American Medial Association, Chicago, IL, US (Feb. 1, 2022) 59(2):205-210.
Patino et al., "A Functional Null Mutation of SCN1B in a Patient with Dravet Syndrome" J. Neurosci. (2009) 29(34):10764-10778.
Rawson et al., "Bacterial and Funcal Coinfection in Individuals with Coronavirus: A Rapid Review to Support COVID-19 Antimicrobial Prescribing" Clinical Infection Diseases (2020) 71:2459-2468.
Shorvon et al., "The treatment of super-refractory status epilepticus: a critical review of available therapies and a clinical treatment protocol" Brain (Oct. 1, 2011) 134(10)2802-2818.
Singh et al., "A Role of SCN9A in Human Epilepsies, As a Cause of Febrile Seizures and as a Potential Modifier of Dravet Syndrome" PLoS Genetics (2009) 5(9):9-12 (pp. 1-14).

(56) References Cited

OTHER PUBLICATIONS

Wikipedia "Marburg acute multiple sclerosis" (Dec. 26, 2020), retrieved on Oct. 9, 2022.

Bewernitz et al., "Electroencephalogram-based pharmacodynamic measures: a review." Int J Clin Pharmacol Ther (2012) 50(3):162-84.

Karceski et al., "Initial treatment of epilepsy in adults." UptoDate. Retrieved from the WayBackMachine on Sep. 21, 2023, https://web/archive.org/web/20210624202606/https://www.uptodate.com/contents/initial-treatment-of-epilepsy-in-adults. Published Jun. 24, 2021.

Maiman et al., "Utility of the Behavior Rating Inventory of Executive Function—Preschool version (BRIEF-P) in young children with epilepsy" Child Neuropsychology (2017)24(7):975-985.

Mayhew et al., "Moving towards meaningful measurement: Rasch analysis of the Morth Start Ambulatory Assessment in Duchenne muscular dystrophy" Developmental Medicine & Child Neurology (2011) 53:535-542.

Tatum et al., "Clinical utility of EEG in diagnosing and monitoring epilepsy in adults." Clinical Neurophys. (2018) 129(5):1056-1082.

Devinsky et al., "Effect of fenfluramine on convulsive seizures in CDKL5 deficiency disorder" Epilepsia (2021) 61(7):E98-E102.

Faingold et al., "Serotonergic agents act on 5-HT3 receptors in the brain to block seizure-induced respiratory arrest in the DBA/1 mouse model of SUDEP" Epilepsy & Behavior (2016) 64:166-170.

Tupal et al., "Prophylaxis of Seizure-Induced Respiratory Arrest (S-IRA) with Fenfluramine in a Mouse Model of SUDEP" 71$^{st}$ American Epilepsy Society Meeting (Nov. 20, 2017) (1 page).

Wang et al., "Neurophysiologic Studies and MRI in Pelizaeus-Merzbacker Disease: Comparison of Classic and Connatal Form" Pediatr. Neurol. (1995) 12:47-53.

Bialer et al., "Progress report on new antiepileptic drugs: A Summary of the Thirteenth Eilat Conerence on New Antiepileptic Drugs and Devices (EILAT XIII)" Epilepsia (2017) 58(2):181-221.

Journal of the Japanese Society of Internatil Medine (2011) 100(2):426-431.

Karussis, "The Diagnosis of multiple sclerosis and the various related demyelinating syndromes A critical review," Journal of Autoimmunity (2014) 48:134-142.

Landmark et al., "Drug interactions involving the new second- and third-generation antiepileptic drugs" Exprt Rev. Neurother. (2010) 20(1):119-140.

Brunherotti et al., "Correlations of Egen Klassifikation and Barthel Index scores with pulmonary function parameters in Cuchenne muscular dystrophy," Heart and Lung (2007) 36:132-139.

Hosseinin-Zare et al., "Effects of experimental traumatic brain injury and impaired glutamate transport on cortical spreading depression" Experimental Neurology (2017) 295:155-161.

\* cited by examiner

METHOD OF TREATING PATIENTS WITH A MUTATION IN CYCLIN-DEPENDENT KINASE-LIKE 5 (CDKL5)

FIELD OF THE INVENTION

This invention relates generally to the field of methods of treatment and, in particular, methods of treating human patients, and more particularly towards treating human patients diagnosed with Rett Syndrome.

BACKGROUND OF THE INVENTION

This invention relates to the treatment of symptoms of Rett syndrome ("RS," sometimes referred to as "Rett's syndrome," "Rett's disorder" or "RTT") using an amphetamine derivative, specifically fenfluramine.

Fenfluramine, i.e. racemic 3-trifluoromethyl-N-ethylamphetamine is an amphetamine derivative having the structure:

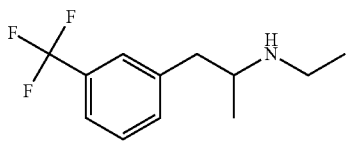 [SMILES: CCNC(C)Cc1cccc(C(F)(F)F)c1]

Systematic (IUPAC) Name (RS)—N-ethyl-1-[3-(trifluoromethyl)phenyl]propan-2-amine Fenfluramine was first marketed in the US in 1973 and had been administered in combination with phentermine to prevent and treat obesity. However, in 1997, it was withdrawn from the US and global market as its use was associated with the onset of cardiac valve fibrosis and pulmonary hypertension. Subsequently, the drug was withdrawn from sale globally and is no longer indicated for use in any therapeutic area. Without being bound by theory, the adverse effects associated with the use of fenfluramine as an anorexic agent are thought to be attributable to the interaction of fenfluramine's major metabolite norfenfluramine with the $5-HT_{2B}$ receptor, which is associated with heart valve hypertrophy.

Fenfluramine is metabolized in vivo into norfenfluramine by cytochrome P450 enzymes in the liver. Cytochrome P450 enzymes such as CYP2D6 and CYP1A2 are primarily responsible for the production of norfenfluramine from fenfluramine in humans. Such metabolism includes cleavage of an N-ethyl group to produce norfenfluramine as shown below.

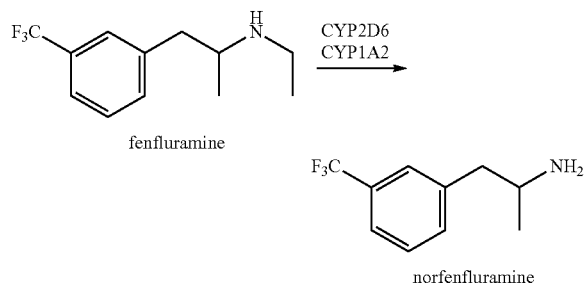

Despite past cardiovascular safety concerns that arose when high doses of fenfluramine were used for treatment of adult obesity, attempts have been made to identify further therapeutic uses for that product, while weighing the known cardiovascular risks of fenfluramine against potential therapeutic benefits. One disorder for which new treatment options are sorely needed is epilepsy, and in particular, epilepsy syndromes which are refractory to known treatments. Epilepsy is a condition of the brain marked by a susceptibility to recurrent seizures. There are numerous causes of epilepsy including, but not limited to birth trauma, perinatal infection, anoxia, infectious diseases, ingestion of toxins, tumors of the brain, inherited disorders or degenerative disease, head injury or trauma, metabolic disorders, cerebrovascular accident and alcohol withdrawal.

Prior to the inventor's work, investigation of fenfluramine's efficacy in epilepsy patients, while showing some initial promise, was far from definitive, and shared a common paradigm, i.e., that fenfluramine's primary effects were on behaviors that caused or induced seizures, not treating or preventing the seizure itself.

For example, Aicardi and Gastaut (*New England Journal of Medicine* (1985), 313:1419 and *Archives of Neurology* (1988) 45:923-925) reported four cases of self-induced photosensitive seizures, i.e., seizures caused by patients purposely staring into bright lights or the sun, that responded to treatment with fenfluramine.

Clemens, in *Epilepsy Research* (1988) 2:340-343 reported a case study wherein a boy suffering pattern sensitivity-induced seizures that were resistant to anticonvulsive treatment was treated with fenfluramine to curb the patient's compulsive seizure-inducing behavior. Fenfluramine reportedly successfully terminated these self-induced seizures and the author concluded that this was because fenfluramine blocked the seizure-sensitive triggering mechanism, i.e., not by treating the seizure itself.

In *Neuropaediatrics*, (1996); 27(4):171-173, Boel and Casaer reported on a study on the effects of fenfluramine on children with refractory epilepsy, all of whom exhibited compulsive seizure-inducing behavior. They observed that when fenfluramine was administered at a dose of 0.5 to 1 mg/kg/day, this resulted in a reduction in the number of seizures experienced by the patients, and concluded that "this drug could have significant anti-epileptic activity in a selected group of young patients with idiopathy or symptomatic generalized epilepsy, namely, children with self-induced seizures." The authors noted that "[i]t may well be that fenfluramine has no direct antiepileptic activity but acts through its effect on the compulsion to induce seizures." Hence the authors seemed to suggest that fenfluramine affected behavior and not the seizure itself.

In a letter to Epilepsia, published in that journal (*Epilepsia*, 43(2):205-206, 2002), Boel and Casaer commented that fenfluramine appeared to be of therapeutic benefit in patients with intractable epilepsy and self-induced seizures. However, the authors did not attribute fenfluramine's efficacy to generalized anti-seizure activity.

A large number of subtypes of epilepsy have been characterized, each with its own unique clinical symptoms, signs, and phenotype, underlying pathophysiology and distinct responses to different treatments. The most recent version, and the one that is widely accepted in the art, is that adopted by the International League Against Epilepsy's ("ILAE") Commission on Classification and Terminology [See e.g., Berg et al., "Revised terminology and concepts for organization of seizures," *Epilepsia*, 51(4):676-685 (2010)]:

I. ELECTROCHEMICAL SYNDROMES (arranged by age of onset):
A. Neonatal period
1. Benign familial neonatal epilepsy (BFNE)
2. Early myoclonic encephalopathy (EME)
3. Ohtahara syndrome
B. Infancy
1. Epilepsy of infancy with migrating focal seizures
2. West syndrome
3. Myoclonic epilepsy in infancy (MEI)
4. Benign infantile epilepsy
5. Benign familial infantile epilepsy
6. Dravet syndrome
7. Myoclonic encephalopathy in non-progressive disorders
C. Childhood
1. Febrile seizures plus (FS+) (can start in infancy)
2. Panayiotopoulos syndrome
3. Epilepsy with myoclonic atonic (previously astatic) seizures
4. Benign epilepsy with centrotemporal spikes (BECTS)
5. Autosomal-dominant nocturnal frontal lobe epilepsy (ADNFLE)
6. Late onset childhood occipital epilepsy (Gastaut type)
7. Epilepsy with myoclonic absences
8. Lennox-Gastaut syndrome
9. Epileptic encephalopathy with continuous spike-and-wave during sleep (CSWS), also known as Electrical Status Epilepticus during Slow Sleep (ESES)
10. Landau-Kleffner syndrome (LKS)
11. Childhood absence epilepsy (CAE)
D. Adolescence—Adult
1. Juvenile absence epilepsy (JAE)
2. Juvenile myoclonic epilepsy (JME)
3. Epilepsy with generalized tonic-clonic seizures alone
4. Progressive myoclonus epilepsies (PME)
5. Autosomal dominant epilepsy with auditory features (ADEAF)
6. Other familial temporal lobe epilepsies
E. Less specific age relationship
1. Familial focal epilepsy with variable foci (childhood to adult)
2. Reflex epilepsies
II. DISTINCTIVE CONSTELLATIONS
A. Mesial temporal lobe epilepsy with hippocampal sclerosis (MTLE with HS)
B. Rasmussen syndrome
C. Gelastic seizures with hypothalamic hamartoma
D. Hemiconvulsion-hemiplegia-epilepsy
E. Epilepsies that do not fit into any of these diagnostic categories, distinguished on the basis of
1. Presumed cause (presence or absence of a known structural or metabolic condition)
2. Primary mode of seizure onset (generalized vs. focal)
III. EPILEPSIES ATTRIBUTED TO AND ORGANIZED BY STRUCTURAL-METABOLIC CAUSES
A. Malformations of cortical development (hemimegalencephaly, heterotopias, etc.)
B. Neurocutaneous syndromes (tuberous sclerosis complex, Sturge-Weber, etc.)
C. Tumor
D. Infection
E. Trauma
IV. ANGIOMA
A. Perinatal insults
B. Stroke
C. Other causes
V. EPILEPSIES OF UNKNOWN CAUSE
VI. CONDITIONS WITH EPILEPTIC SEIZURES NOT TRADITIONALLY DIAGNOSED AS FORMS OF EPILEPSY PER SE
A. Benign neonatal seizures (BNS)
B. Febrile seizures (FS)

Part V of the ILAE classification scheme underscores the fact that the list is far from complete, and that there are still subtypes of epilepsy that have not yet been fully characterized, or that remain unrecognized as distinct syndromes. One among these more recently identified epileptic syndromes is Rett syndrome which is a progressive neurologic disorder in which seizures are a prominent feature. Rett syndrome is caused by mutations in the methyl-CpG-binding protein 2 (MeCP2) gene on chromosome Xq28. Mutations in JMJD1C can also contribute to the development of the syndrome and intellectual disability (*Genet Med.* 2016 April; 18(4): 378-385). MeCP2 is highly expressed in the brain and is especially abundant in post-mitotic neurons. Most mutations are sporadic and rarely inherited. Moreover, mutations in males are frequently lethal in utero to hemizygous males or result in severe infantile encephalopathy because of complete absence of functional MeCP2. In contrast, females are heterozygous for the mutation with approximately one-half of the cells expressing the mutant MECP2 allele but with the other half expressing a functional allele, because of X chromosome inactivation. Thus, RTT is a disease that is almost exclusively seen in females.

Approximately 95% of individuals with a Rett diagnosis have a confirmed mutation in MECP2. Hundreds of mutations in MECP2 have been identified, from which eight hotspot mutations account for more than 60% of all cases. Of the many documented disease-causing mutations, missense mutations are particularly informative because they accurately pinpoint important functional domains. The distribution of RTT missense mutations is markedly nonrandom, being largely confined to regions of the gene that encode the DNA-binding domain (MBD) and the NCoR/SMRT Interaction Domain (NID). Functionally, MeCP2 has been implicated in several cellular processes on the basis of its reported interaction with more than 40 binding partners, including transcriptional co-repressors, transcriptional activators, and other factors involved in gene activation and expression. However, researchers recently tested the hypothesis that the single dominant function of MeCP2 is to physically connect DNA with the NCoR/SMRT complex which they did by removing almost all amino-acid sequences except the methyl-CpG binding and NCoR/SMRT interaction domains. They found that mice expressing truncated MeCP2 lacking both the N- and C-terminal regions (approximately half of the native protein) are phenotypically near-normal, and that the minimal protein is able to prevent or reverse neurological symptoms when introduced into MeCP2-deficient mice. (Tillotson, R., *Nature.* 2017 Oct. 19; 550 (7676):398-401).

The molecular effects of MeCP2 seem to be primarily mediated by its MBD and NID regions, but the functional effects of MeCP2 are region-specific and cell-type-specific (for example, selective for exhibitory or inhibitory neuron subtypes). The functional effects of MeCP2 loss depend on the disruption of excitatory/inhibitory imbalance within neuronal circuits, and neuronal circuits seem to be particularly sensitive to MeCP2 loss from inhibitory neurons which suggests that the molecular effects of MeCP2 are not equal across functional cell classes and functional brain regions. (Chapleau, et al., *Curr Clin Pharmacol.* 2013; 8(4): 358-369) Thus differential deleterious effects of the MeCP2 mutation in neuronal development, maturation, plasticity and function, with overt changes in synaptic function including reduced synaptic plasticity and changes in basal inhibitory and excitatory synaptic transmission and multiple neuronal signaling systems are affected. Phenotypically RTT presents as a complex neurodevelopmental and seizure disorder associated with intellectual disability in females.

Clinically, an affected female presents as normal until, at sometime between the ages of 6-25 months, neurological and mental development begin to stagnate accompanied by the regression of acquired skills. One typical sign of Rett syndrome is the slowing of the growth of head circumference. Other hallmark symptoms of RTT include significant verbal and nonverbal communication deficits, increased muscle tone (spasticity), and the loss of motor skills and coordination, including purposeful hand use, which is replaced by almost constant stereotypical movements such as hand wringing, rubbing, or washing movements. Other brain dysfunctions are marked by autistic behavior, dementia, apraxia of gait, loss of facial expression, and ataxia. Behavior and mood disorders, such as, for example, depression, anxiety, and fearful behaviors and aggression are also recognized to occur in some Rett syndrome patients.

Autistic behaviors or characteristics include, by way of non-limiting example, stereotyped movements, social withdrawal and averted gaze, repetitive behaviors and obsessions, anxiety, attention deficit, hyperactivity, depression, a reclusive personality, and the inability to understand feelings. However, social dysfunction seems to be temporary in nature and social contact and eye gaze are markedly improved after about three years of age in many patients.

Autonomic abnormalities are also a feature in many patients, resulting in disordered breathing, pupil dilation, gastro-esophageal reflux and bowel motility problems, hypotrophic, cold blue feet and/or hands, severe constipation, oropharyngeal dysfunction, and cardiac abnormalities, including tachycardia, prolonged corrected QT intervals, and sinus bradycardia. Following the stage of stagnation and decline there is an intermediate period of relatively stable mental status, sometimes lasting several decades, which is followed by further neurological degradation, marked mainly by spasticity of the lower limbs and epilepsy. Disordered breathing can manifest as hyperventilation, breath-holding, gulping air, disordered breathing during sleep, obstructive sleep apnea and central sleep apnea. Some features of disordered breathing, such as breath holding or gulping of air also appear to have an association with autism spectrum disorders, for example, obsessive compulsive stereotypies. Gastaut, et al. [J Autism Dev Disord. 1987 September; 17(3) 391-406] reported some beneficial effects of fenfluramine in a subset of patients from the results of an open label study in 8 children with compulsive respiratory stereotypies. This illustrates that in some Rett symptoms it may be difficult to classify the cause of the dysfunction as purely related to one receptor or neuronal signaling system and may be in some instances two or more dysfunctions may be involved.

Seizures occur commonly in Rett patients, diagnosed as either typical or atypical in presentation, and often develop after the initial period of decline: 34% of patients experience seizures between 2 and 3 years of ages, increasing to about 60% in patients between 5 and 10 and increasing steadily thereafter to about 86% in patients 30 years or older. Approximately one-third of Rett epilepsies are treatment resistant.

Most recognized MECP2 mutations and deletions are associated with seizures, and one correlation of seizures to genotype found a range of between 50% and 78% among the mutation types. One study reported that seizures are related to statistically significant worsening of ratings of severity of disease, ambulation and hand use. Recently, mutations in another X-linked gene, cyclin-dependent kinase-like 5 (CDKL5) located in Xp22, have been identified in patients affected by a RTT-like phenotype or the early-onset of seizures variant of RTT (the so-called Hanefeld variant) (Scala et al., *J. Med. Genet*, 42:103-107 (2005)).

Individuals with Rett syndrome are often unable to provide fully for their own needs, with many requiring life-long medical care and 24 hour a day supportive care as they grow older. Most Rett syndrome patients live well into adulthood. Thus, the costs of medical and related services such as special education and/or institutional care for patients with Rett syndrome are high. Rett syndrome currently has no cure, and treatment is largely directed at improving symptoms. For example, anticonvulsant therapeutics may be used to help reduce the frequency and/or severity of seizures; unfortunately, the results obtained with many anticonvulsants are inadequate, yielding only partial cessation of seizures at best. Furthermore, many anticonvulsants such as clobazam and clonazepam have undesirable side effects, which are particularly acute and prominent in pediatric patients. As such, a need remains for new methods of treating seizures in Rett syndrome.

Different subtypes of epilepsy are triggered by different stimuli, are controlled by different biological pathways, and have different causes, whether genetic, environmental, and/or due to disease or injury of the brain. Thus, the teachings relating to one epileptic subtype are not necessarily applicable to any other subtype. Of particular importance is the fact that there are a large number of compounds that are used to treat different types of epilepsy, and different epilepsy subtypes respond differently to different anticonvulsant drugs. That is, while a particular drug may be effective against one form of epilepsy, it may be wholly ineffective against others, or even contra-indicated due to exacerbation of symptoms, such as worsening the frequency and severity of the seizures. As a result, efficacy of a particular drug with respect to a particular type of epilepsy is wholly unpredictable, and the discovery that a particular drug is effective in treating in treating a type of epilepsy for which that drug was not previously known to be effective is nearly always surprising, even in cases where the drug is known to be effective against another epilepsy type.

Diagnosis

RTT is a syndrome and hence its diagnosis is based on the presence of specific clinical symptoms, signs, and laboratory tests. RTT is typically identified by a triad of features including multiple types of seizures, mental retardation or regression and abnormal EEG with generalized slow spike and wave discharges.

The diagnostic criteria for classical and variant RS (Hagberg publication):

Inclusion Criteria*

*The first three clinical criteria may not be applicable to severely affected females; other criteria will not apply to those who are mildly affected and are only identified due to positive findings of mutations in MECP2.

Apparently normal pre- and perinatal history
Psychomotor development normal during the first 6 months (may be delayed from birth)
Normal head circumference at birth
Postnatal deceleration of head growth (most individuals)
Loss of purposeful hand skills between 0.5-2.5 years
Stereotypic hand movements Evolving social withdrawal, communication dysfunction, loss of acquired speech, cognitive impairment
Impaired or deteriorating locomotion
Supportive Criteria
Breathing disturbances while awake
Bruxism
Impaired sleeping pattern from early infancy
Abnormal muscle tone accompanied by muscle wasting and dystonia
Peripheral vasomotor disturbances
Progressive scoliosis, or kyphosis
Growth retardation
Hypotrophic, small and cold feet and/or hands
Exclusion Criteria
Organomegaly or other evidence of a storage disorder
Retinopathy, cataract, or optic atrophy
History of perinatal or postnatal brain damage
Identifiable inborn error of metabolism or neurodegenerative disorder
Acquired neurological disorder due to severe infection or head trauma
Treatment There is no approved pharmaceutical or biological treatment for Rett syndrome. Many different treatments are currently being investigated in the treatment of this disorder and most treatment modalities have shown little success. Experimental treatments target either the mutation or other targets downstream of the MeCP2 mutation induced dysfunction.

Therapeutic genetic approaches under study include strategies to activate the second X-chromosome that is silenced by inactivation; gene therapies such as genome editing, mRNA editing and therapy, protein replacements, and therapy with read-through compounds (such as certain aminoglycosides that counteract premature stop codons generated by nonsense mutations). Drug therapies under study are in the use of agents that act on neurotransmitter signaling pathways, that modulate BDNF and/or IGF-1 signaling, that act on metabolic pathways including improvement of mitochondrial function and that modulate neuronal ion channels.

Brain-derived neurotrophic factor (BDNF) is a member of the neurotrophins family of growth factors that plays an important role in the survival of neurons, and in the formation and maturation of synapses. BDNF also contributes to long-term potentiation (LTP), enhancement of neurotransmitter release, and alterations of channel function and spine morphology. BDNF/TrkB modulators being studied in Rett syndrome, include LM22A-4, a BDNF loop-domain mimetic, and fingolimod, a S1P modulator which increases BDNF levels, and 7,8 DHF (7,8-dihydroxyflavone, including carbamate prodrug forms R7 and R13 disclosed in U.S. Pat. No. 9,682,948) as TrkB selective agonists.

Other agents that affect BDNF/TrkB signaling pathways or receptors include CX-546, an ampakine positive allosteric modulator; and Copaxone, an immunomodulator known to increase secretion of BNDF. Disruption of MECP2 function is associated with increased levels of PTP1B in RTT animal models and PTP1B is a negative regulator of tyrosine kinase TRKB. Compounds CPT157633 and UA0713 (an ursolic acid derivative) are PTP1B inhibitors that increase tyrosine phosphorylation of TrkB in the brain and thus augment BDNF signaling. IGF-1, which is indirectly regulated by MECP2, has been shown to enhance the maturation and maintenance of synapses, both known to be impaired in Rett syndrome and to ameliorate several Rett-like features in mouse models. Mecanserin and trofenatide (a brain-penetrant truncated peptide having the first three amino acids of IGF-1) are presently being evaluated in clinical trials in RTT.

Certain specific serotonin receptor modulators are being studied in stereotypies: 5-(2-fluorophenyl)-N,N-dimethyl-1,2,3,4-tetrahydronaphthalen-2-amine (5-FPT) as a partial agonist of serotonin receptor subtypes 5-HT$_{1A}$ and 5-HT$_7$. A brain-penetrant selective agonist at 5-HT$_7$, 6-(4-Biphenyl-2-yl-piperazin-1-yl)-hexanoic acid 4-cyano-benzylamide (LP-211) has been shown to rescue brain mitochondrial dysfunction in a Rett mouse model. Phenytoin, a sodium channel blocker has been studied in mouse models as a treatment for cardiac arrhythmias associated with RTT.

A2-73 (or Avanex2-73) is a sigma-1 receptor agonist in clinical trials for treatment of Alzheimer's disease. The compound has shown activity in mouse models of RTT and was reported to have received a grant to enter clinical trials for RTT.

Treatment of seizures is important in itself in Rett syndrome, but seizure control or amelioration may also affect other outcomes such as cognitive decline and use of speech. Sodium valproate (VPA) is most commonly administered at seizure onset, followed by carbamazepine and phenobarbital. Monotherapy is the first line treatment option in most patients followed by polypharmacy for resistant seizures. VPA and CBZ proved to be equally effective in Rett patients who presented seizures within the typical age range (4-5 years), while lamotrigine (LTG) has proved to be effective for patients in whom epilepsy started later. The ketogenic diet or vagal nerve stimulation may be useful in some patients with RTT who are refractory to medical treatment or as an adjunct to medication. Marketed drugs that have been employed in animal models to assess activity in treating other RTT symptoms mediated by neurotransmitter pathways include desipramine, clenbuterol, citalopram, L-DOPA in combination with benserazide, choline, ketamine, sarizotan and midazolam. Statins and glucocorticoids, such as corticosterone, are used in treating metabolic symptoms and triheptanoin is being studied in reducing oxidative stress and mitochondrial dysfunction.

Despite the severity of RTT symptoms, there is currently no standard evidence-based treatment for the disease. Pharmaceutical treatments directed to control or amelioration of symptoms of Rett syndrome, such as, for example, control or reduction of seizures, of sleep disorders, of constipation, of gastro-esophageal reflux, of anxiety and of depression.

Rett syndrome at present has no cure; disease symptoms can be treated with medicines, surgery, and physical and speech therapy with varying degrees of success. Most people with Rett syndrome live into middle age and beyond. They will usually need care throughout their lives. There is accordingly a dire and long-felt need to provide an improved method for treating or ameliorating the symptoms and progressive decline of Rett syndrome.

SUMMARY OF THE INVENTION

According to a first aspect of the present invention, there is provided a method of treating and/or preventing one or more symptoms of Rett syndrome in a patient comprising administering an effective dose to a patient of fenfluramine alone or in combination with one or more drugs as described here.

According to a further aspect of the present invention, there is provided a method of treating, preventing and/or ameliorating seizures in a patient diagnosed with Rett syndrome comprising administering an effective dose to a patient of fenfluramine alone or in combination with one or more drugs as described here.

In another aspect of the present invention, there is provided a method of treating, preventing and/or ameliorating disordered breathing in a patient diagnosed with Rett Syndrome comprising administering an effective dose to a patient of fenfluramine alone or in combination with one or more drugs as described herein. In an embodiment, an effective dose of fenfluramine is co-administered with sarizotan, clenbuterol or NLX-101 to treat disordered breathing in a patient with Rett syndrome.

In a further aspect of the present invention, there is provided a method of treating, preventing and/or ameliorating autism spectrum behaviors and/or symptoms in a patient diagnosed with Rett syndrome comprising administering an effective dose to a patient of fenfluramine alone or in combination with one or more drugs as described here.

A still further aspect of the present invention, there is provided a method of treating, preventing and/or ameliorating behavior and mood disorders in a patient diagnosed with Rett syndrome comprising administering an effective dose to a patient of fenfluramine alone or in combination with one or more drugs as described herein. In embodiments fenfluramine treatment ameliorates aggressive or self-injurious behaviors, anxiety or depression.

A further aspect of the present invention, there is provided a method of improving cognitive deficits in a patient diagnosed with Rett syndrome comprising administering an effective dose to a patient of fenfluramine alone or in combination with one or more drugs as described herein.

In still another aspect of the present invention, there is provided a method of improving sleep onset and/or duration in a patient diagnosed with Rett syndrome comprising administering an effective dose to a patient of fenfluramine alone or in combination with one or more drugs as described herein.

According to a further aspect of the present invention, there is provided a method of treating a patient that exhibits a mutation in one or more of a gene selected from the group consisting of MeCP2, CDLK5 and JMJD1C by administering to that patient an effective dose of fenfluramine.

A still further aspect of this invention contemplates a method for stimulating one or more 5-HT receptors in the brain of a patient by administering an effective dose of fenfluramine or a pharmaceutically acceptable salt thereof to that patient. Illustrative one or more 5-HT receptors are selected from the group consisting of one or more of 5-$HT_1$, 5-$HT_{1A}$, 5-$HT_{1B}$, 5-$HT_{1C}$, 5-$HT_{1D}$, 5-$HT_{1E}$, 5-$HT_{1F}$, 5-$HT_2$, 5-$HT_{2A}$, 5-$HT_{2B}$, 5-$HT_{2C}$, 5-$HT_3$, 5-$HT_4$, 5-$HT_5$, 5-$HT_{5A}$, 5-$HT_{5B}$ 5-$HT_6$, and 5-$HT_7$. In addition there may be non-5-HT binding in the brain including Sigma, M1 muscarinic, B-adrenergic. In a preferred embodiment, the one or more targets are selected from the group consisting of the sigma-1 receptor, the 5-$HT_{1A}$ receptor, the 5-$HT_{1D}$ receptor, the 5-$HT_{2A}$ receptor, the 5-$HT_{2C}$ receptor, and the SERT transporter. In some embodiments, a therapeutically effective dose of a 5-$HT_{1D}$, 5-$HT_{2A}$, 5-$HT_{2C}$ or sigma-1 receptor agonist is administered.

Yet another aspect of the invention contemplates co-administration of an effective dose of one or more co-therapeutic antiepileptic agents with the fenfluramine wherein the co-therapeutic agents can be selected from the group consisting of cannabidiol, carbamazepine, ethosuximide, phenytoin, fosphenytoin, lamotrigine, levetiracetam, phenobarbital, progabide, topiramate, stiripentol, valproic acid, valproate, verapamil, vigabtrin and benzodiazepines such as clobazam, clonazepam, diazepam, ethyl loflazepate, lorazepam, midazolam. Use of a pharmaceutically acceptable salt or base of a co-therapeutic agent is also contemplated.

A further aspect of the invention contemplates co-administration of agents of use in treating symptoms other than seizure in RTT may also be co-administered to improve one or more non-seizure symptoms of Rett syndrome. Such therapeutic agents may be useful to modulate targets downstream of the MeCP2 mutation. In some embodiments the agents for co-administration will target neuronal transmission and signaling pathways; growth factor signaling pathways, metabolic pathways, or modulate ion channels.

An aspect of the invention is a method of treating or preventing the symptoms of Rett syndrome (RTT) in a patient diagnosed with RTT comprising administering an effective dose of fenfluramine or pharmaceutically acceptable salt to the patient, wherein the dose is administered in an amount in the range of from 10.0 mg/kg/day to about 0.05 mg/kg/day, or about 1.0 mg/kg/day to about 0.1 mg/kg/day, or about 0.8 mg/kg/day to about 0.2 mg/kg/day, or administered at 60 mg or less, or 30 mg or less, or 20 mg or less, or 10 mg or less and may be administered with, or in the absence of, the administration of any other pharmaceutically active compound.

In another aspect of the invention, the method is carried out wherein the effective dose is administered in a form selected from the group consisting of oral, injectable, transdermal, buccal, inhaled, nasal, rectal, vaginal, or parental, and wherein the formulation is oral, the formulation may be liquid which may be a solution or a suspension may be present within a container closed with a cap connected to a syringe graduated to determine the volume extracted from the container wherein the volume extracted relates to the amount of fenfluramine in a given liquid volume of formulation e.g. one millimeter of formulation contains 2.5 mg of fenfluramine. In another aspect of the invention, the method is administered in a solid oral formulation in the form of a tablet, capsule, lozenge, or sachet.

The method may be carried out as a co treatment with a different pharmaceutically active compound. The method may be carried out in a process wherein the patient is first then subjected to a series of tests to confirm diagnoses of RTT.

Another aspect of the invention is a kit for treating Rett syndrome (RTT) in a patient diagnosed with RTT wherein the kit comprises a formulation comprising a pharmaceutically acceptable carrier and an active ingredient comprising fenfluramine and instructions for treating a patient diagnosed with RTT by administering the formulation to the patient. In yet another aspect, wherein the fenfluramine is in an oral liquid or a solid oral dosage form or a transdermal patch; and the kit further comprises instructions for treating a patient diagnosed with RTT by administering the formulation to the patient.

In another aspect of the invention, the kit consists of an oral liquid formulation in a container and a syringe with instructions, wherein the concentration of the fenfluramine in the liquid is calibrated based on calibrations on the syringe and includes calibrations wherein a milliliter of solution equates to a known amount of fenfluramine such as 0.1 mg, 0.2 mg etc., to 1.0 mg.

In another aspect of the invention, the kit includes instructions relating to dosing the patient based on patient weight and volume of solution based on the concentration of fenfluramine in the solution.

Another aspect of the invention is a use of a fenfluramine composition in treating and or preventing symptoms of Rett syndrome (RTT) and a patient diagnosed with RTT which use may include placing the fenfluramine in a liquid solution and withdrawing that liquid solution into a graduated syringe.

An aspect of the invention includes a formulation comprising a therapeutically effective dose of a 5-HT$_{1D}$, 5-HT$_{2A}$, 5-HT$_{2C}$ or sigma-1 receptor agonist or a pharmaceutically acceptable salt thereof for use in treating, preventing and/or ameliorating symptoms in a patient diagnosed with Rett syndrome wherein the 5-HT$_{1D}$, 5-HT$_{2A}$, 5-HT$_{2C}$ or sigma-1 receptor agonist is formulated with a pharmaceutically acceptable carrier for administering an effective dose(s) of less than about 5.0 mg/kg/day to about 0.1 mg/kg/day.

In another aspect of the invention the symptoms are chosen from the group consisting of seizures, disordered breathing, autism spectrum behaviors, stereotypies, cognitive impairment, and sleep disturbances.

In another aspect of the invention the agonist is fenfluramine or a pharmaceutically acceptable salt, base or acid thereof.

In another aspect of the invention the effective dose is selected from the group consisting of 40 mg or less, 30 mg or less, and 20 mg or less, and wherein the effective dose is administered in a dosage form selected from the group consisting of forms for oral, injectable, transdermal, inhaled, nasal, rectal, vaginal and parenteral delivery.

In another aspect of the invention fenfluramine is the only active ingredient administered to the patient.

In another aspect of the invention the effective dose of the 5-HT$_{1D}$, 5-HT$_{2A}$, HT$_{2C}$ or formulation-1 receptor agonist is co-administered with one or more co-therapeutic anti-epileptic agents selected from the group consisting of carbamazepine, cannabidiol, ethosuximide, fosphenytoin, lamotrigine, levetiracetam, phenobarbital, topiramate, stiripentol, valproic acid, valproate, verapamil, vigabatrin and benzodiazepines such as clobazam, clonazepam, diazepam, lorazepam, and midazolam and a pharmaceutically acceptable salt or base thereof.

In another aspect of the invention the effective dose of agonist is co-administered with one or more co-therapeutic agents selected from the group consisting of LM22A-4, fingolimod, copaxone, CX-546, 5-FPT, 7,8-dihydroxyflavone, R7, R13, LP-211, clenbuterol, IGF-1; trofenatide, NLX-101, sarizotan, ketamine, NO-711, lovastatin, corticosterone, CNF1, triheptanoin, EPI-732, benserazide, L-DOPA, citalopram and mecanserin.

In another aspect of the invention the agonist is administered with a co-therapeutic agent is selected from stiripentol, cannabidiol, and a combination of both.

In another aspect of the invention the co-therapeutic agent is administered in an amount sufficient to increase fenfluramine blood levels by 50% or more relative to fenfluramine blood levels obtained in the absence of the co-administration of the co-therapeutic agent, and further wherein blood levels of a metabolite of fenfluramine are decreased relative to levels of a flenfluramine metabolite obtained in the absence of the co-administration of the co-therapeutic agent.

An aspect of the invention includes a kit for treating one or more symptoms of Rett syndrome (RTT) in a patient diagnosed with a MeCP2 mutation, comprising: a container comprising a plurality of doses of a formulation comprising a pharmaceutically acceptable carrier and an active ingredient comprising fenfluramine; instructions for treating the patient diagnosed with the mutation by withdrawing the formulation from the container and administering the formulation to the patient.

Another aspect of the kit the formulation is an oral solution comprising 2.5 milligram of fenfluramine in each milliliter of liquid solution; and the instructions indicate dosing the patient based on patient weight and volume of oral solution administered.

Another aspect of the kit the formulation is a solid oral formulation selected from the group consisting of: a tablet, a disintegrating tablet, a capsule, a modified release tablet or capsule, a lozenge, and a sachet.

Another aspect of the kit said formulation is provided as a modified release tablet or capsule.

In another aspect of the invention the effective dose is of fenfluramine is administered in an amount of between 0.2 to 0.8 mg/kg/day, to a maximum of 30 mg/day, and the dose is oral.

A specific aspect of the invention is a formulation comprising a therapeutically effective dose of fenfluramine or a pharmaceutically acceptable salt thereof for use in ameliorating symptoms in a patient with Rett syndrome wherein the formulation is administered to a patient in an oral liquid dosage form once daily or twice daily in an amount of 0.2 to 0.8 mg/kg/day up to a maximum of 30 mg/kg/day with variations of ±5%, 10% 20%, or 50%.

These and other objects, advantages, and features of the invention will become apparent to those persons skilled in the art upon reading the details of the methods of treating symptoms of Rett Syndrome as more fully described below.

DETAILED DESCRIPTION OF THE INVENTION

Before the present method, kits and formulations are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a seizure" includes a plurality of such seizures and reference to "the formulation" includes reference to one or more formulations and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

To avoid doubt, the term "prevention" of seizures means the total or partial prevention (inhibition) of seizures. Ideally, the methods of the present invention result in a total prevention of seizures. However, the invention also encompasses methods in which the instances of seizures are decreased in frequency by at least 40%, at least 50%, at least 55%, at least 60%, at least 65%, at least 70%, at least 75%, at least 80%, at least 85%, or at least 90%. In addition, the invention also encompasses methods in which the instances of seizures are decreased in duration or severity by at least 40%, at least 50%, at least 55%, at least 60%, at least 65%, at least 70%, at least 75%, at least 80%, at least 85%, or at least 90%.

Seizures are a common symptom of Rett syndrome. It has surprisingly been found that seizures exhibited by patients with Rett syndrome, convulsive and nonconvulsive, can be suppressed by treatment in accordance with a method of the present invention. A type of epilepsy or epileptic encephalopathy may be separately diagnosed or found to be concurrent with Rett syndrome.

In the context of the present invention, the term "seizure" is used to encompass photosensitive or induced seizures, convulsive or nonconvulsive seizures, as well as some or all other types of seizures experienced by patients with epilepsy and/or Rett syndrome.

In some instances, mutations occur in genes linked to epilepsy in X-linked intellectual disability. Mutations may occur in one or more of the following genes: ARHGEF9, ARX, ATP6AP2, ATP7A, ATRX, CASK, CDKL5, CUL4B, DCX, FGD1, GPC3, GRIA3, HSD17B10, IQSEC2, KDM5C, MAGT1, MECP2, OFD1, OPHN1, PAK3, PCDH19, PHF6, PLP1, PQBP1, RAB39B, SLC16A2, SLC9A6, SMC1A, SMS, SRPX2, SYN1, SYP.

Without being bound by theory, fenfluramine has been known to be a serotonin releaser of (5-HT) in the brain due to disruption of its vesicular storage and to inhibit serotonin reuptake by reversing the action of the serotonin transporter (SERT). Fenfluramine has activity at one or more 5-HT receptors selected from the group consisting of the $5\text{-}HT_{1A}$ receptor, the $5\text{-}HT_{1D}$ receptor, the $5\text{-}HT_{1E}$ receptor, the $5\text{-}HT_{2A}$ receptor, the $5\text{-}HT_{2C}$ receptor, the $5\text{-}HT_{5A}$ receptor, and the $5\text{-}HT_7$ receptor, (see, for example, commonly owned US published application 2018/0092864). However, until the present invention was made, it was not known that fenfluramine's mechanism of action made it suitable for the treatment of symptoms associated with Rett syndrome (RTT).

Thus, according to a still further aspect of the present invention, there is provided a method of stimulating one or more 5-HT receptors in the brain of a patient by administering an effective dose of fenfluramine to said patient, said one or more 5-HT receptors being selected from one or more of $5\text{-}HT_1$, $5\text{-}HT_{1A}$, $5\text{-}HT_{1B}$, $5\text{-}HT_{1C}$, $5\text{-}HT_{1D}$, $5\text{-}HT_{1E}$, $5\text{-}HT_{1F}$, $5\text{-}HT_2$, $5\text{-}HT_{2A}$, $5\text{-}HT_{2B}$, $5\text{-}HT_{2C}$, $5\text{-}HT_3$, $5\text{-}HT_4$, $5\text{-}HT_5$, $5\text{-}HT_{5A}$, $5\text{-}HT_{5B}$ $5\text{-}HT_6$, and $5\text{-}HT_7$ amongst others. In certain embodiments of this aspect of the invention, the patient has been diagnosed with Rett Syndrome.

In an embodiment, an effective dose of fenfluramine provides $5\text{-}HT_{2C}$ receptor stimulation (agonism) for the treatment of some neurological disorders, such as autism spectrum disorders which manifest as stereotypies, compulsions and self-injurious behaviors in Rett syndrome. In a further embodiment, an effective dose of fenfluramine provides $5\text{-}HT_{1A}$ and $5\text{-}HT_7$ receptor stimulation (agonism) for the treatment of disordered breathing in a patient with Rett syndrome. In yet another embodiment, an effective dose of fenfluramine provides $5\text{-}HT_{1D}$, $5\text{-}HT_{2A}$ and $5\text{-}HT_{2C}$ and sigma-1 receptor stimulation (agonism) for treatment of seizures in a patient with Rett syndrome. In a further embodiment stimulation of $5\text{-}HT_{2C}$ receptors in the basal ganglia provides for the regulation of repetitive motion and in the cingulate gyrus mediates the effects of neurotransmitters on compulsive-type behaviors, thus reducing stereotypies associated with Rett syndrome.

In embodiments of the invention, any effective dose of fenfluramine can be employed. However, surprisingly low doses of fenfluramine have been found by the inventors to be effective, particularly for inhibiting or eliminating seizures in Rett syndrome patients.

DOSE BY WEIGHT (MG/KG/DAY) Thus in some cases, in a preferred embodiment of the invention, a daily dose of less than about 10 mg/kg/day, such as less than about 10 mg/kg/day, less than about 9 mg/kg/day, less than about 8 mg/kg/day, less than about 7 mg/kg/day, less than about 6 mg/kg/day, less than about 5 mg/kg/day, less than about 4 mg/kg/day, less than about 3.0 mg/kg/day, less than about 2.5 mg/kg/day, less than about 2.0 mg/kg/day, less than about 1.5 mg/kg/day, less than about 1.0 mg/kg/day, such as about 1.0 mg/kg/day, about 0.95 mg/kg/day, about 0.9 meg/kg/day, about 0.85 mg/kg/day, about 0.85 mg/kg/day, about 0.8 mg/kg/day, about 0.75 mg/kg/day, about 0.7 mg/kg/day, about 0.65 mg/kg/day, about 0.6 mg/kg/day, about 0.55 mg/kg/day, about 0.5 mg/kg/day, about 0.45 mg/kg/day, about 0.4 mg/kg/day, about 0.350 mg/kg/day, about 0.3 mg/kg/day, about 0.25 mg/kg/day, about 0.2 mg/kg/day, about 0.15 mg/kg/day to about 0.1 mg/kg/day, about 0.075 mg/kg/day, about 0.05 mg/kg/day, about 0.025 mg/kg/day, about 0.0225 mg/kg/day, about 0.02 mg/kg/day, about 0.0175 mg/kg/day, about 0.015 mg/kg/day, about 0.0125 mg/kg/day, or about 0.01 mg/kg/day is employed.

Put differently, a preferred dose is less than about 5 to about 0.05 mg/kg/day. In some cases the dose is less than about 1.0 mg/kg/day to 0.1 mg/kg/day, such as less than about 0.9 mg/kg/day, less than about 0.8 mg/kg/day, less than about less than about 0.7 mg/kg/day, less than about 0.6 mg/kg/day to about 0.05 mg/kg/day, less than about 1.0 mg/kg/day to about 0.1 mg/kg/day, less than about 0.8 mg/kg/day to about 0.2 mg/kg/day, less than about 0.3 mg/kg/day to about 0.01 mg/kg/day, or less than about 0.2 mg/kg/day to about 0.01 mg/kg/day.

As indicated above, the dosing is based on the weight of the patient. However, for convenience the dosing amounts may be preset such as in the amount of 1.0 mg, 2.5 mg, 5 mg, 10 mg, 15 mg, 20 mg, 30 mg, or 40 mg. In certain instances, the dosing amount may be preset such as in the amount of about 0.25 mg to about 5 mg, such as about 0.25 mg, about 0.5 mg, about 0.75 mg, about 1.0 mg, about 1.25 mg, about 1.5 mg, about 1.75 mg, about 2.0 mg, about 2.25 mg, about 2.5 mg, about 2.75 mg, about 3.0 mg, about 3.25 mg, about 3.5 mg, about 3.75 mg, about 4.0 mg, about 4.25 mg, about 4.5 mg, about 4.75 mg, or about 5.0 mg.

In general, the smallest dose which is effective should be used for the particular patient.

The dosing amounts described herein may be administered one or more times daily to provide for a daily dosing amount, such as once daily, twice daily, three times daily, or four or more times daily, etc.

In certain embodiments, the dosing amount is a daily dose of 30 mg or less, such as 30 mg, about 29 mg, about 28 mg, about 27 mg, about 26 mg, about 25 mg, about 24 mg, about 23 mg, about 22 mg, about 21 mg, about 20 mg, about 19 mg, about 18 mg, about 17 mg, about 16 mg, about 15 mg, about 14 mg, about 13 mg, about 12 mg, about 11 mg, about 10 mg, about 9 mg, about 8 mg, about 7 mg, about 6 mg, about 5 mg, about 4 mg, about 3 mg, about 2 mg, or about 1 mg. In general, the smallest dose which is effective should be used for the particular patient. In some cases, the dose is well below the dosing used in weight loss.

ROUTES OF ADMINISTRATION The dose of fenfluramine administered according to the methods of the present invention can be administered systemically or locally. Methods of administration may include administration via enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. In certain embodiments, it may be desirable to administer one or more compounds of the invention locally to the area in need of treatment. This may be achieved, for example, by local infusion during, topical application, by injection, by means of a catheter, by means of a suppository, or by means of an implant, said implant being of a porous, non-porous, or gelatinous material, including membranes, such as sialastic membranes, or fibers.

DOSAGE FORMS/ROUTE OF ADMIN The dose of fenfluramine administered in the methods of the present invention can be formulated in any pharmaceutically acceptable dosage form including, but not limited to (a) oral dosage forms such as tablets including orally disintegrating tablets, capsules, and lozenges, oral solutions or syrups, oral emulsions, oral gels, oral films, buccal liquids, powder e.g. for suspension, and the like; (b) injectable dosage forms; (c) transdermal dosage forms such as transdermal patches, ointments, creams; (c) inhaled dosage forms; and/or (e) nasally, (f) rectally, (g) vaginally administered dosage forms.

DOSAGE FORM/FREQUENCY OF ADMIN Such dosage forms can be formulated for once a day administration, or for multiple daily administrations (e.g. 2, 3 or 4 times a day administration). Alternatively, for convenience, dosage forms can be formulated for less frequent administration (e.g., monthly, bi-weekly, weekly, every fourth day, every third day, or every second day), and formulations which facilitate extended release are known in the art.

DOSAGE FORMS/PREPARATION, COMPONENTS The dosage form of fenfluramine employed in the methods of the present invention can be prepared by combining fenfluramine or a pharmaceutically acceptable salt thereof with one or more pharmaceutically acceptable diluents, carriers, adjuvants, and the like in a manner known to those skilled in the art of pharmaceutical formulation.

ORAL DOSAGE FORMS/SUITABLE FORMULATION TYPES & COMPONENTS THEREOF In some embodiments, formulations suitable for oral administration can include (a) liquid solutions, such as an effective amount of the compound dissolved in diluents, such as water, or saline; (b) capsules, sachets or tablets, each containing a predetermined amount of the active ingredient (fenfluramine), as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can include the active ingredient in a flavor, usually sucrose and acacia or tragacanth, as well as pastilles including the active ingredient in an inert base, such as gelatin and glycerin, or sucrose and acacia, emulsions, gels, and the like containing, in addition to the active ingredient, such excipients as are described herein.

ORAL DOSAGE FORMS/EXCIPIENTS For an oral solid pharmaceutical formulation, suitable excipients include pharmaceutical grades of carriers such as mannitol, lactose, glucose, sucrose, starch, cellulose, gelatin, magnesium stearate, sodium saccharine, and/or magnesium carbonate. For use in oral liquid formulations, the composition may be prepared as a solution, suspension, emulsion, or syrup, being supplied either in solid or liquid form suitable for hydration in an aqueous carrier, such as, for example, aqueous saline, aqueous dextrose, glycerol, or ethanol, preferably water or normal saline. If desired, the composition may also contain minor amounts of non-toxic auxiliary substances such as wetting agents, emulsifying agents, or buffers.

By way of illustration, the fenfluramine composition can be admixed with conventional pharmaceutically acceptable carriers and excipients (i.e., vehicles) and used in the form of aqueous solutions, tablets, capsules, elixirs, suspensions, syrups, wafers, and the like. Such pharmaceutical compositions contain, in certain embodiments, from about 0.1% to about 90% by weight of the active compound, and more generally from about 1% to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

Formulations suitable for topical administration may be presented as creams, gels, pastes, or foams, containing, in addition to the active ingredient, such carriers as are appropriate. In some embodiments the topical formulation contains one or more components selected from a structuring agent, a thickener or gelling agent, and an emollient or lubricant. Frequently employed structuring agents include long chain alcohols, such as stearyl alcohol, and glyceryl ethers or esters and oligo(ethylene oxide) ethers or esters thereof. Thickeners and gelling agents include, for example, polymers of acrylic or methacrylic acid and esters thereof, polyacrylamides, and naturally occurring thickeners such as agar, carrageenan, gelatin, and guar gum. Examples of emollients include triglyceride esters, fatty acid esters and amides, waxes such as beeswax, spermaceti, or carnauba wax, phospholipids such as lecithin, and sterols and fatty acid esters thereof. The topical formulations may further include other components, e.g., astringents, fragrances, pigments, skin penetration enhancing agents, sunscreens (e.g., sunblocking agents), etc.

Particular formulations of the invention are in an oral liquid form. The liquid can be a solution or suspension and may be an oral solution or syrup, which is included in a bottle with a syringe graduated in terms of milligram amounts which will be obtained in a given volume of solution. The liquid solution makes it possible to adjust the volume of solution for appropriate dosing of small children, who can be administered fenfluramine in an amount anywhere from 1.25 mg to 30 mg and any amount between in 0.25 milligram, increments and thus administered in amounts of 1.25 mg, 1.5 mg, 1.75 mg, 2.0 mg, etc.

A specific aspect of the invention is a treatment carried out to relieve symptoms of Rett by the administration of only fenfluramine. However, the fenfluramine may be co-administered with other known pharmaceutical drugs such as a co-therapeutic agent selected from the group consisting of carbamazepine, ethosuximide, fosphenytoin, lamotrigine, levetiracetam, phenobarbital, progabide, topiramate, stiripentol, valproic acid, valproate, verapamil, and benzodiazepines such as clobazam, clonazepam, diazepam, ethyl loflazepate, lorazepam, midazolam and a pharmaceutically acceptable salt or base thereof.

The co-therapeutic agents have recommended dosing amounts. Those recommended dosing amounts are provided within the most current version of the Physician's Desk Reference (PDR) or online at (emedicine.medscape.com/) both of which are incorporated herein by reference specifically with respect to the co-therapeutic agents listed above and more specifically with respect to the dosing amounts recommended for those drugs.

In connection with the present invention, the co-therapeutic agent can be used in the recommended dosing amount or can be used in a range of from $100^{th}$ to 100 times $\frac{1}{10}$ to 10 times $\frac{1}{5}$ to 5 times $\frac{1}{2}$ to twice the recommended dosing amount or any incremental $\frac{1}{10}$ amount in between those ranges.

As a specific example of a combination of co-therapeutic agents with fenfluramine, the co-therapeutic agent may be any one of or all three of stiripentol, clobazam, and valproate. The fenfluramine may be administered in the amount of 0.8 mg/kg of patient body weight and co-administered with 3500 mg of stiripentol, 20 mg of clobazam, and 25 mg per kg of valproate. Each of those amounts may be increased to twice, three times, five times, or ten times that amount or decreased by 10%, 50%, or 75%.

An aspect of the invention includes a kit for treating and or preventing symptoms of RTT in a patient diagnosed with RTT, the kit comprising:
 a container holding a liquid formulation of fenfluramine;
 a dispensing device connected to the container and configured to withdraw the liquid formulation from the container; and
 instructions for administering the liquid formulation to a patient in order to treat RTT.

In alternate embodiments, the dispensing device may be a syringe or graduated pipette useful for delivering varying doses of the fenfluramine liquid. In another embodiment, the dispensing device is a metered dosing device capable of dispensing a fixed volume of fenfluramine liquid. In one exemplary embodiment, the dose delivered by the metered dosing device is adjustable.

The formulation may be a solution or suspension and is prepared such that a given volume of the formulation contains a known amount of active fenfluramine.

For example, in one embodiment of this aspect, the dispensing device is a syringe is graduated in one millimeter increments and the liquid fenfluramine formulation is characterized such that one millimeter in volume of formulation includes precisely one milligram of fenfluramine. In this manner, the patient may be correctly dosed with a desired milligram dosage of fenfluramine based on a volume of liquid formulation administered to the patient orally.

In alternate embodiments, the dispenser is a syringe connected to the container and configured to withdraw the liquid formulation from the container, wherein the syringe is marked with levels of graduation noting volume of formulation withdrawn, or a metered dose dispenser for delivering a predetermined volume of the formulation to said patient, or a metered dispensing device calibrated to deliver a predetermined volume of the liquid, permitting convenient, consistent, and accurate dosing.

In a method of the present invention, fenfluramine can be employed as a monotherapy in the treatment of Rett Syndrome. Alternatively, fenfluramine can be co-administered in combination with one or more pharmaceutically active agents, which may be provided together with the fenfluramine in a single dosage formulation, or separately, in one or more separate pharmaceutical dosage formulations. Where separate dosage formulations are used, the subject composition and ore or more additional agents can be administered concurrently, or at separately staggered times, i.e., sequentially.

In one embodiment, the agents are co-therapeutic agents, such as anticonvulsants (also referred to anti-epileptic drugs, or AEDs). Preferred AED co-therapeutic agents can be selected from the group consisting of carbamazepine, cannabidiol, ethosuximide, fosphenytoin, lamotrigine, levetiracetam, phenobarbital, progabide, topiramate, stiripentol, valproic acid, valproate, verapamil, and benzodiazepines such as clobazam, clonazepam, diazepam, ethyl loflazepate, lorazepam, midazolam. Use of a pharmaceutically acceptable salt of a co-therapeutic agent is also contemplated.

Notably, fenfluramine's therapeutic effects appear to be independent of any significant placebo effects. In general, the effects of the placebo arm in epilepsy clinical trials are generally quite positive, making an efficacious therapy difficult to validate. While seizure-freedom rates on placebo are quite low (0-2.8%), rates on 50%-responder rates on placebo are quite a bit larger (4-27%) (Burneo et al., 2002; Cramer et al., 1999; Guekht et al., 2010; Rheims et al., 2008; Zaccara et al., 2015), and may be higher yet due to a statistically significant publication bias in epilepsy public trials (Beyenburg et al., 2010). Although the placebo phenomenon may be partially attributable to normal disease progression (Goldenholz et al., *Ann. Neurol.* 2015 SEP; 78(3): 329-336. Published online 2015 Jul. 29, doi 10.1002/ana.24470), and its magnitude influenced by a number of factors, it is verifiable, and likely due to positive or negative expectations of patients and of investigators. See generally Goldenholz et al., Response to Placebo in Clinical Epilepsy Trials—Old Ideas and New Insights *Epilepsy Res.* 2016 May; 122: 15-25, Published online 2016 Feb. 10. doi: 10.1016/j.eplepsyres.2016.02.002.

Unexpectedly, the results obtained in double-blinded fenfluramine clinical trials effectively match those from open label studies, which leads to the surprising conclusion that fenfluramine's efficacy is free of any placebo effect, unlike the majority of more conventional anti-epileptics.

This is an unexpected and surprising result providing improvements in the reliability and robustness of fenfluramine's efficacy as an antiseizure medication in Rett syndrome.

Thus, according to a further aspect of the present invention, there is provided a method of preventing or reducing seizures in a patient diagnosed with Rett syndrome by administering to that patient a therapeutically effective dose of fenfluramine, whereby seizures are prevented or reduced. In various embodiments of this aspect, the instances of seizures are decreased by at least 50%, at least 60%, at least 70%, at least 80% or at least 90%.

Thus, according to a further aspect of the present invention, there is provided a method of treating a patient that exhibits a mutation in one, some or all of the genes described herein by administering to that patient an effective dose of a 5-$HT_{2C}$ agonist. In certain embodiments of this aspect of the invention, the patient has been diagnosed with Rett syndrome. In some embodiments, the a 5-$HT_{2C}$ agonist is fenfluramine, or a pharmaceutically acceptable salt, base or acid thereof.

Fenfluramine has been known to inhibit serotonin reuptake and to trigger the release of serotonin in the brain due to disruption of its vesicular storage. Data from more recent studies provide evidence that fenfluramine is a positive allosteric modulator of the sigma-1 receptor. The Sigma-1 receptor (S1R) protein, which serves as a molecular chaperone and functional modulator, is involved in restoring homeostasis and modulation of many biological mechanism associated with neurodegeneration. Thus sigma-1 agonists are useful in providing neuroprotection and restoration and maintenance of neuronal signaling pathways. The results provided here indicate a high degree of efficacy in the treatment of Rett syndrome using fenfluramine to dramatically reduce and in some cases completely eliminate seizures from patients being treated, improving disordered breathing, improving cognition and slowing or halting cognitive decline In some aspects, described herein is a method of treating a patient diagnosed with Rett syndrome, comprising administering to the patient a therapeutically effective dose of a 5-$HT_{2C}$ agonist, thereby reducing seizures in the patient. In some embodiments, the method further comprises repeating the administering over a period of days until the patient exhibits a reduction from baseline in convulsive seizure frequency of 40% or more.

In some embodiments of these methods, the epilepsy is concurrent with Rett syndrome. In some embodiments of these methods, seizures are a symptom of Rett syndrome.

In some embodiments, the 5-$HT_{2C}$ agonist is fenfluramine or a pharmaceutically acceptable salt, base or acid thereof, in an amount of 0.2 mg/kg/day or more, up to 30 mg/day, and further comprising administering a co-therapeutic agent, and repeating the administering of the co-therapeutic agent and fenfluramine over a period of weeks until the patient exhibits a reduction from baseline in convulsive seizure frequency of 60% or more.

In some embodiments, the method further comprises repeating the administering over a period of days until the patient exhibits an increase from baseline in an average time between convulsive seizures of eight hours or more. In some embodiments, the 5-$HT_{2C}$ agonist is fenfluramine or a pharmaceutically acceptable salt, base or acid thereof in an amount of 0.2 mg/kg/day or more, up to 30 mg/day, and the method further comprises administering a co-therapeutic agent, and repeating the administering of the co-therapeutic agent and fenfluramine over a period of weeks until the patient exhibits an increase from baseline in average time between convulsive seizures of one week or more.

In some embodiments, the method further comprises repeating the administering over a period of days until the patient exhibits a reduction from baseline in a seizure type experienced by the patient. In some embodiments of the method, the 5-HT2C agonist is fenfluramine or a pharmaceutically acceptable salt, base or acid thereof in an amount of 0.2 mg/kg/day or more, up to 30 mg/day, and further comprising administering a co-therapeutic agent, and repeating the administering of the co-therapeutic agent and fenfluramine over a period of weeks until the patient exhibits a reduction from baseline in two types of seizures.

In some embodiments, the 5-HT2C agonist is fenfluramine or a pharmaceutically acceptable salt, base or acid thereof.

In some embodiments, the method further comprises administering a co-therapeutic agent selected from the group consisting of: cannabidiol, carbamazepine, ethosuximide, fosphenytoin, lamotrigine, levetiracetam, phenobarbital, stiripentol, topiramate, valproic acid, valproate, verapamil, and benzodiazepines such as clobazam, clonazepam, diazepam, lorazepam, and midazolam and a pharmaceutically acceptable salt or base thereof. In some embodiments, the co-therapeutic agent is a combination of stiripentol, valproate and clobazam. In some embodiments, the co-therapeutic agent is cannabidiol. In some embodiments, fenfluramine is the only active ingredient administered to the patient. In some embodiments, fenfluramine is the only anti-epileptic drug administered to the patient. In some embodiments, the administering is over a period of months, and the co-therapeutic agent is clobazam.

In some embodiments, the patient diagnosed with Rett syndrome was previously determined non-responsive when treated with an anti-epileptic drug or the patient's response to an anti-epileptic drug diminished over time. In some aspects, provided herein is a formulation for use in treating a patient in a selected patient population diagnosed with Rett syndrome, the formulation comprising a therapeutically effective dose of fenfluramine or a pharmaceutically acceptable salt, base or acid thereof, wherein the formulation is for use with a patient previously determined non-responsive when treated with cannabidiol or stiripentol, or the patient's response to cannabidiol or stiripentol diminished over time, and wherein the use is repeated over a period of days until the patient exhibits a reduction from baseline in convulsive seizure frequency.

In some embodiments, a particular type of seizure is reduced. In some embodiments, two seizure types are reduced. In some embodiments, three seizure types are reduced. In some embodiments, the seizure type reduced is selected from the group consisting of non-convulsive seizures, generalized seizures, myoclonic seizures, absence seizures, and febrile seizures, or any combination thereof. In some embodiments, the method further comprises recording seizure types experienced daily by the patient in an electronic diary. In some embodiments, the method further comprises repeating the administering of the 5-$HT_{2C}$ agonist until the patient improves two or more symptoms selected from the group consisting of convulsive seizures, ataxias, gait abnormalities, sleep disturbances and cognitive impairment.

In some embodiments, the method further comprises repeating the administering of the fenfluramine in an amount of 0.2 mg/kg/day or more up to 30 mg/day until the patient exhibits a 90% reduction from baseline in seizure frequency.

In some embodiments, the method further comprises repeating the administering until the patient is seizure free for a period of 1 day. In some embodiments, the method further comprises repeating the administering until the patient is seizure free for a period of 6 months. In some embodiments, the method further comprises repeating the administering until the patient is permanently seizure free.

Thus, according to a still further aspect of the present invention, there is provided a method of stimulating or modulating one or more targets in the brain of a patient by administering a therapeutically effective dose of fenfluramine to said patient, wherein said one or more targets are selected from the group consisting of a chaperone protein, a bioamine transporter (BAT), and a 5-HT receptor, wherein
  (a) the chaperone protein is selected from the group consisting of the sigma-1 protein and the sigma-2 protein; and
  (b) the BAT is selected from the serotonin transporter (SERT), the norepinephrine transporter (NET), and the dopamine transporter (SERT); and
  (c) the 5-HT receptor is in a family of receptors selected from the group consisting of 5-HT1, 5-HT2, 5-HT3, 5-HT4, 5-HT5, 5-HT6, and 5-HT7; wherein
    (i) the 5-HT receptor in the 5-HT1 receptor family is selected from the group consisting of 5-HT1A, 5-HT1B, 5-HT1C, 5-HT1D, 5-HT1E, and 5-HT1F;
    (ii) the 5-HT receptor in the 5-HT2 receptor family is selected from the group consisting of 5-HT2A, 5-HT2B, and 5-HT2C;
    (iii) the 5-HT receptor in the 5-HT3 receptor family is selected from the group consisting of 5-HT3A and 5-HT3B;
    (iv) the 5-HT receptor is 5-HT4;
    (v) the 5-HT receptor in the 5-HT5 receptor family is selected from the group consisting of 5-HT5A or 5-HT5B; and
    (vi) the 5-HT receptor in the 5-HT7 family is 5-HT7,
whereby the activity of the one or more targets in the brain of the patient are stimulated or modified.

In one embodiment, the stimulation of the one or more targets in a Rett syndrome patient provides improvement in one or more symptoms of the disease chosen from reductions in (i) convulsive seizure frequency, ataxia, gait abnormality, sleep disturbances and cognitive impairment. Changes in ataxia can be measured for example by a clinical scale (SARA) developed by Schmitz-Hübsch et al. (*Movement Disorders* 2007, 22:1633-7) which assesses a range of different impairments in cerebellar ataxia. The scale is made up of 8 items related to gait, stance, sitting, speech, finger-chase test, nose-finger test, fast alternating movements and heel-shin test. Cognitive assessments in Rett syndrome patients may be made using, for example, the BRIEF scale for measuring executive function or other measures such as those described by Ahca et al., in Child Neuropsychology, 21(5):693-715 (2014).

In a preferred embodiment, the one or more targets are selected from the group consisting of the sigma-1 receptor, the $5\text{-HT}_{1A}$ receptor, the $5\text{-HT}_{1D}$ receptor, the $5\text{-HT}_{2A}$ receptor, the $5\text{-HT}_{2C}$ receptor, and the SERT transporter.

In embodiments of the invention, any effective dose of fenfluramine can be employed. However, surprisingly low doses of fenfluramine have been found by the inventors to be efficacious, particularly for inhibiting or eliminating seizures in Rett syndrome patients. Thus, in preferred embodiments of the invention, the maximum daily dose is not more than about 30 mg/day, with a daily dose of less than about 1.0 mg/kg/day, 0.9 mg/kg/day, 0.8 mg/kg/day, 0.7 mg/kg/day, 0.6 mg/kg/day, 0.5 mg/kg/day, about 0.4 mg/kg/day, about 0.3 mg/kg/day, about 0.25 mg/kg/day or about 0.2 mg/kg/day to about 0.1 mg/kg/day, about 0.05 mg/kg/day, or about 0.01 mg/kg/day is employed. Put differently, a preferred dose is not more than about 30 mg/day, and less than about 1 to about 0.01 mg/kg/day. Such a dose is less than the daily dose of fenfluramine suggested for administration to achieve weight loss.

The dose of fenfluramine administered in the methods of the present invention can be formulated in any pharmaceutically acceptable dosage form including, but not limited to oral dosage forms such as tablets including orally disintegrating tablets, capsules, lozenges, oral solutions or syrups, oral emulsions, oral gels, oral films, buccal liquids, powder e.g. for suspension, and the like; injectable dosage forms; transdermal dosage forms such as transdermal patches, ointments, creams; inhaled dosage forms; and/or nasally, rectally, vaginally administered dosage forms. Such dosage forms can be formulated for once a day administration, or for multiple daily administrations (e.g. 2, 3 or 4 times a day administration).

The dosage form of fenfluramine employed in the methods of the present invention can be prepared by combining fenfluramine with one or more pharmaceutically acceptable diluents, carriers, adjuvants, and the like in a manner known to those skilled in the art of pharmaceutical formulation.

Fenfluramine can be employed to treat a patient who has previously been treated with an anticonvulsant, e.g., as described herein, such as stiripentol or cannabidiol. In some instances, the patient is diagnosed with Rett syndrome that is refractory to treatment with a particular anticonvulsant agent e.g., as described herein. In certain instances, the anticonvulsant agent is a modulator of neuronal GABA(A) receptors, such as stiripentol. By refractory to anticonvulsant agent (e.g., stiripentol or cannabidiol) is meant that the frequency of convulsive seizures (FCS) is not significantly reduced in the patient in response to therapy (e.g., monotherapy) with the anticonvulsant agent. In some cases, a significant reduction in FCS is a 10% or greater reduction in mean monthly convulsive seizures, such as 15% or greater, 20% or greater, 25% or greater, 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, 95% or greater, or 99% or greater reduction. In certain instances, the subject method is a method of preventing or treating seizures in a patient diagnosed with Rett syndrome refractory to stiripentol by administering to that patient a therapeutically effective dose of fenfluramine, whereby seizures are prevented or reduced. In various embodiments of this aspect, the instances of seizures (e.g., mean monthly convulsive seizures) are decreased by at least 50%, at least 55%, at least 60%, at least 65%, at least 70%, at least 75%, at least 80%, at least 85%, at least 90%, or at least 95%.

In some aspects, provided herein is a method of reducing convulsive seizure frequency in a human patient diagnosed with Rett syndrome, comprising administering to the patient a therapeutically effective dose of fenfluramine or a pharmaceutically acceptable salt, base, acid or amine thereof, and repeating the administering over a period of a day or days, weeks, months or years until the patient exhibits a significant reduction (e.g., 40% to 80% or even greater) from baseline in convulsive seizure frequency. In some embodiments of the method, convulsive seizures are completely eliminated for 10 days or more, 20 days or more, 30 days or more, 50 days or more, 100 days or more. In some embodiments of the method, the repeating administration continues over a period of 4 weeks or more until a significant reduction from baseline in convulsive seizure frequency is observed. In some embodiments of the method, convulsive seizures are completely eliminated for 10 days or more, 20 days or more, 30 days or more, 50 days or more, 100 days or more. In some embodiments of the method, repeating the administering occurs over a period of a day or days, or over a period of weeks, or over a period of months or over a period of years. Administration may be daily, once a day, twice a day, three times a day or four times a day. In some embodiments, the dose is provided to the patient at a level of 0.2 mg/kg/day or 0.8 mg/kg/day up to a maximum of 30 mg per day. In some embodiments, the fenfluramine or pharmaceutically acceptable salt, base, acid or amine thereof is fenfluramine hydrochloride. In some embodiments, the fenfluramine hydrochloride is in a liquid formulation at a concentration of 1.25 mg/ml, 2.5 mg/ml or 5 mg/ml provided at twelve-hour intervals twice a day using an oral syringe graduated for precise measurement of the dose of the liquid formulation, administered alone or with another antiepileptic drug as a co-therapeutic agent. In some embodiments, the therapeutically effective dose of fenfluramine or a pharmaceutically acceptable salt, base, acid or amine thereof is twice per day in a liquid formulation in an amount of 0.2 mg/kg/day to 0.8 mg/kg/day, and the repeating administration continues until the patient exhibits a reduction from baseline in convulsive seizure frequency. Pharmaceutical compositions and formulations for use in practicing the subject methods are also provided.

In some aspects, provided herein is a method of reducing an average time between seizures in a human patient diagnosed with Rett syndrome, comprising administering to the patient a therapeutically effective dose of fenfluramine or a pharmaceutically acceptable salt, base, acid or amine thereof, and repeating the administering over a period of days until the patient exhibits an increase from baseline in average time between convulsive seizures of 6 hours, 12 hours, 18 hours, one day, multiple days, a week, multiple weeks or more. In some embodiments, a patient diagnosed with Rett syndrome is treated by administering to the patient a therapeutically effective dose of fenfluramine or a pharmaceutically acceptable salt, base, acid or amine thereof, and repeating the administering over a period of a day or days, or over a period of weeks, months or years until the patient exhibits an increase from baseline in average time between convulsive seizures of 6 to 23 hours or more, 1 to 6 days or more, 1 to 3 weeks or more, 1 to 11 months or more, one year or more, or seizures are completely eliminated for 10 days or more, 20 days or more, 30 days or more, 50 days or more, 100 days or more. In some embodiments, the administering is repeated over a period of days until the patient exhibits an increase from baseline in average time between convulsive seizures of 4 hours or more, 5 hours or more, 6 hours or more, 7 hours or more, 8 hours or more, 9 hours or more, 12 hours or more, 15 hours or more, 18 hours or more, or 24 hours or more. In some embodiments, repeating the administering occurs over a period of a day or days, or over a period of weeks, or over a period of months or over a period of years. In some embodiments in which the repeat administration is daily, the administration is once a day, twice a day, three times a day or four times a day. In some embodiments, the dose is provided to the patient at a level of 0.2 mg/kg/day or 0.8 mg/kg/day up to a maximum of 30 mg per day. In some embodiments, the patient exhibits an increase from baseline in average time between convulsive seizures of 6 to 23 hours or more, 1 to 6 days or more, 1 to 3 weeks or more, 1 to 11 months or more, one year or more, or seizures are completely eliminated for 10 days or more, 20 days or more, 30 days or more, 50 days or more, 100 days or more. In some embodiments, the fenfluramine or pharmaceutically acceptable salt, base, acid or amine thereof is fenfluramine hydrochloride. In some embodiments, the fenfluramine hydrochloride is in a liquid formulation at a concentration of 1.25 mg/ml, 2.5 mg/ml or 5 mg/ml. In some embodiments, the fenfluramine hydrochloride in a liquid formulation at a concentration of 1.25 mg/ml, 2.5 mg/ml or 5 mg/ml provided at twelve-hour intervals twice a day using an oral syringe graduated for precise measurement of the dose of the liquid formulation, administered alone or with another antiepileptic drug as a co-therapeutic agent. In some embodiments of the method, the repeating administration continues over a period of 4 weeks or more until an increase from baseline in average time between convulsive seizures of 6 to 23 hours or more, 1 to 6 days or more, 1 to 3 weeks or more, 1 to 11 months or more, one year or more, or seizures are completely eliminated for 10 days or more, 20 days or more, 30 days or more, 50 days or more, 100 days or more is observed. In some embodiments, the therapeutically effective dose of fenfluramine or a pharmaceutically acceptable salt, base, acid or amine thereof is twice per day in a liquid formulation in an amount of 0.2 mg/kg/day to 0.8 mg/kg/day, and the repeating administration continues until an increase from baseline in average time between convulsive seizures of 6 to 23 hours or more, 1 to 6 days or more, 1 to 3 weeks or more, 1 to 11 months or more, one year or more, or seizures are completely eliminated for 10 days or more, 20 days or more, 30 days or more, 50 days or more, 100 days or more is observed. Pharmaceutical compositions and formulations for use in practicing the subject methods are also provided.

In some aspects, provided herein is a method of reducing a particular type of seizure in a human patient diagnosed with Rett syndrome, by administering to the patient a therapeutically effective dose of fenfluramine or a pharmaceutically acceptable salt, base, acid or amine thereof, and repeating the administering over a period of a day or days, or over a period of weeks, months or years until the patient exhibits a reduction from baseline in seizures of a particular type. The reduction may be of one, two, three or multiple specific types of seizures. In some embodiments, two seizure types are reduced. In some embodiments, three seizure types are reduced. In some embodiments, the seizure type reduced is a non-convulsive seizure. In some embodiments, the seizure type reduced is selected from the group consisting of generalized seizures, myoclonic seizures, absence seizures, and febrile seizures, or any combination thereof. In some embodiments, the seizure types reduced are selected from the group consisting photosensitive and self-induced seizures. In some embodiments, the seizure types were recorded daily in an electronic diary. In some embodiments, repeating the administering occurs over a period of a day or days, or over a period of weeks, or over a period of months or over a period of years. In some embodiments in which the repeat administration is daily, the administration is once a day, twice a day, three times a day or four times a day. In some embodiments, the dose is provided to the patient at a level of 0.2 mg/kg/day or 0.8 mg/kg/day up to a maximum of 30 mg per day. In some embodiments, the patient exhibits a reduction from baseline in a particular seizure type of 50% or more, 60% or more, 70% or more, 80% or more, 90% or more, 95% or more. In some embodiments, the particular seizure type is completely eliminated for 10 days or more, 20 days or more, 30 days or more, 50 days or more, 100 days or more. In some embodiments, the fenfluramine or pharmaceutically acceptable salt, base, acid or amine thereof is fenfluramine hydrochloride. In some embodiments, the fenfluramine hydrochloride is in a liquid formulation at a concentration of 1.25 mg/ml, 2.5 mg/ml or 5 mg/ml provided at twelve-hour intervals twice a day using an oral syringe graduated for precise measurement of the dose of the liquid formulation, administered alone or with another anti-epileptic drug as a co-therapeutic agent. In some embodiments of the method, the repeating administration continues over a period of 4 weeks or more until a reduction from baseline in a particular seizure type experienced by the patient is observed. In some embodiments, the repeating administration continues until a particular seizure type experienced by the patient is eliminated for a period of 10 days or more. In some embodiments, the repeating administration continues over a period of 4 weeks or more by administering the fenfluramine twice per day in a liquid formulation in an amount of 0.2 mg/kg/day to 0.8 mg/kg/day until a particular seizure type experienced by the patient is eliminated over a period of 10 days or more. Pharmaceutical compositions and formulations for use in practicing the subject methods are also provided.

In some aspects, provided herein is a method of reducing dosage of a concomitant anti-epileptic drug (AED) in a human patient diagnosed with Rett syndrome, by administering to the patient a therapeutically effective dose of fenfluramine or a pharmaceutically acceptable salt, base, acid or amine thereof, and repeating the administering over a period of days until the patient exhibits a significant reduction in seizure frequency while reducing the dose of one or more concomitant anti-seizure drugs (AEDs) from baseline by 40% or more mg per day to 30 mg per day. In some embodiments, the administering is repeated over a period of days while the dose of one or more concomitant AEDs is reduced from baseline by 40% or more, while maintaining the efficacy of the treatment. In some embodiments of the method, the concomitant AED is reduced in increments while monitoring efficacy of the treatment. In some embodiments of the method, the incremental reduction continues over a period of days or weeks. In some embodiments of the method, the reduction continues until the patient no longer receives a dose of the concomitant AED. In some embodiments, the method further comprises administering a co-therapeutic agent. In some embodiments, the fenfluramine hydrochloride is in a liquid formulation at a concentration of 1.25 mg/ml, 2.5 mg/ml or 5 mg/ml provided at twelve-hour intervals twice a day using an oral syringe graduated for precise measurement of the dose of the liquid formulation, administered alone or with another anti-epileptic drug as a co-therapeutic agent. Pharmaceutical compositions and formulations for use in practicing the subject methods are also provided.

In some aspects, provided herein is a method of adjusting dose of stiripentol and/or cannabidiol in a human patient diagnosed with Rett syndrome, by administering, to a patient receiving stiripentol and/or cannabidiol, a therapeutically effective dose of fenfluramine or a pharmaceutically acceptable salt, base, acid or amine thereof, and increasing the fenfluramine dosage to 0.4 mg/kg/day for days 18-24 of fenfluramine therapy; and thereafter increasing the daily dosage to 0.5 mg/kg/day; provided that the total dosage of fenfluramine does not exceed 20 mg/day. In some aspects, provided herein is a method of dosing a patient with fenfluramine, wherein the patient is receiving stiripentol therapy and commencing fenfluramine therapy for treating a form of epilepsy, by administering to the patient receiving stiripentol an initial dosage of fenfluramine of 0.2 mg/kg/day for the first seven days of fenfluramine therapy; increasing the initial dosage to 0.4 mg/kg/day for days 18-24 of fenfluramine therapy; and thereafter increasing the daily dosage to 0.5 mg/kg/day; provided that the total dosage of fenfluramine does not exceed 20 mg/day. In some aspects, provided herein is a method of dosing a patient with fenfluramine, wherein the patient is receiving cannabidiol therapy and commencing fenfluramine therapy for treating a form of epilepsy, by administering to the patient receiving cannabidiol an initial dosage of fenfluramine of 0.2 mg/kg/day for the first seven days of fenfluramine therapy; increasing the initial dosage to 0.4 mg/kg/day for days 18-24 of fenfluramine therapy; and thereafter increasing the daily dosage to 0.5 mg/kg/day; provided that the total dosage of fenfluramine does not exceed 20 mg/day. In some embodiments of these methods, the epilepsy is concurrent with Rett syndrome. In some embodiments of these methods, seizures are a symptom of Rett syndrome. In some embodiments of these methods, the titration provides increased tolerability of the combination of stiripentol and fenfluramine. In some embodiments of these methods, the titration provides increased tolerability of the combination of cannabidiol and fenfluramine. In some embodiments, the patient is already receiving one or more co-therapeutic agents in addition to stiripentol. In some embodiments, the patient is already receiving one or more co-therapeutic agents in addition to cannabidiol. In some embodiments, the one or more co-therapeutic agents are clobazam or valproate or both. In some embodiments of the method, the patient is administered the therapeutically effective dose for a period of weeks/months/years and the reduction from baseline is sustained for a period of weeks/months/years. In some embodiments in which the repeat administration is daily, the administration is once a day, twice a day, three times a day or four times a day. In some embodiments, the dose is provided to the patient at a level of 0.2 mg/kg/day or 0.8 mg/kg/day up to a maximum of 30 mg per day. In some embodiments, the patient exhibits a reduction from baseline in convulsive seizure frequency of 50% or more, 60% or more, 70% or more, 80% or more, 90% or more, 95% or more. In some embodiments, seizures are completely eliminated for 10 days or more, 20 days or more, 30 days or more, 50 days or more, 100 days or more. In some embodiments, the fenfluramine or pharmaceutically acceptable salt, base, acid or amine thereof is fenfluramine hydrochloride. In some embodiments, the fenfluramine hydrochloride is in a liquid formulation at a concentration of 1.25 mg/ml, 2.5 mg/ml or 5 mg/ml provided at twelve-hour intervals twice a day using an oral syringe graduated for precise measurement of the dose of the liquid formulation, administered alone or with another antiepileptic drug as a co-therapeutic agent. Pharmaceutical compositions and formulations for use in practicing the subject methods are also provided.

In some aspects, provided herein is a method of treating a selected epileptic patient population, wherein the epileptic patient population is selected based on a determination that the epileptic patients have previously been non-responsive when treated with stiripentol. In some embodiments, the method comprises selecting the patient based on a previously failed treatment with stiripentol, based on lack of efficacy or tolerability. The method comprises determining/identifying a patient or a population of patients diagnosed with Rett syndrome, who previously had been non-responsive when treated with stiripentol or the patient's response to stiripentol diminished with increasing time. The selected population of patients is then treated by administering, to each identified patient, a therapeutically effective dose of fenfluramine or a pharmaceutically acceptable salt, base, acid or amine thereof; and repeating the administering over a period of a day or days, or over a period of weeks, months or years, until the patient exhibits a reduction from baseline in convulsive seizure frequency. In some embodiments of the method, the patient is administered the therapeutically effective dose for a period of weeks/months/years and the reduction from baseline is sustained for a period of weeks/months/years. In some embodiments in which the repeat administration is daily, the administration is once a day, twice a day, three times a day or four times a day. In some embodiments, the dose is provided to the patient at a level of 0.2 mg/kg/day or 0.8 mg/kg/day up to a maximum of 30 mg per day. In some embodiments, the patient exhibits a reduction from baseline in convulsive seizure frequency of 50% or more, 60% or more, 70% or more, 80% or more, 90% or more, 95% or more. In some embodiments, seizures are completely eliminated for 10 days or more, 20 days or more, 30 days or more, 50 days or more, 100 days or more. In some embodiments, the fenfluramine or pharmaceutically acceptable salt, base, acid or amine thereof is fenfluramine hydrochloride. In some embodiments, the fenfluramine hydrochloride is in a liquid formulation at a concentration of 1.25 mg/ml, 2.5 mg/ml or 5 mg/ml provided at twelve-hour intervals twice a day using an oral syringe graduated for precise measurement of the dose of the liquid formulation, administered alone or with another antiepileptic drug as a co-therapeutic agent. In some embodiments of the method, the repeating administration continues over a period of 4 weeks or more until a reduction in convulsive seizure frequency is observed. In some embodiments, the repeating administration continues until the patient's seizures are eliminated for a period of 10 days or more. In some embodiments, the repeating administration continues until a reduction in convulsive seizure frequency is observed. In some embodiments, the repeating administration continues over a period of 4 weeks or more by administering the fenfluramine twice per day in a liquid formulation in an amount of 0.2 mg/kg/day to 0.8 mg/kg/day until the patient's seizures are eliminated over a period of 10 days or more. Pharmaceutical compositions and formulations for use in practicing the subject methods are also provided.

The formulation may include flavoring and coloring agents or may be completely devoid of any excipient materials beyond those necessary to dissolve the fenfluramine in the liquid which may be water.

In some embodiments of the method, fenfluramine is the only active ingredient administered to the patient. In some embodiments, the method further comprises administering a co-therapeutic agent. In some embodiments, the fenfluramine is adjunctive therapy and is co-administered with a second therapeutic agent. Any second therapeutic agents of interest may be utilized. In some cases, the second therapeutic agent is selected from the group consisting of cannabidiol, carbamazepine, ethosuximide, fosphenytoin, lamotrigine, levetiracetam, phenobarbital, topiramate, stiripentol, valproic acid, valproate, verapamil, and benzodiazepines such as clobazam, clonazepam, diazepam, lorazepam, and midazolam and a pharmaceutically acceptable salt or base thereof.

Aspects of the subject methods include identifying a patient previously treated unsuccessfully with stiripentol who will benefit from treatment with fenfluramine according to the methods described herein. Fenfluramine can then be employed to treat the patient either as a subsequent monotherapy or as a co-therapy with stiripentol. In some cases, the patient can be monitored for a reduction in instances of seizures (e.g., mean monthly convulsive seizures) relative to that observed under prior treatment with stiripentol.

Fenfluramine can be employed to treat a patient who has previously been treated with cannabidiol. In some instances, the patient is diagnosed with Rett syndrome that is refractory to treatment with cannabidiol. By refractory to cannabidiol is meant that the frequency of convulsive seizures (FCS) is not significantly reduced in the patient in response to therapy (e.g., monotherapy) with cannabidiol (CBD). In some cases, a significant reduction in FCS is a 10% or greater reduction in mean monthly convulsive seizures, such as 15% or greater, 20% or greater, 25% or greater, 30% or greater, 35% or greater, 40% or greater, or 45% or greater reduction. In certain instances, the subject method is a method of preventing or treating seizures in a patient diagnosed with Rett syndrome refractory to treatment with cannabidiol by administering to that patient a therapeutically effective dose of fenfluramine, whereby seizures are prevented or reduced. In various embodiments of this aspect, the instances of seizures (e.g., mean monthly convulsive seizures) are decreased by at least 50%, at least 60%, at least 70%, at least 80% or at least 90%. Aspects of the subject methods include identifying a patient previously treated unsuccessfully with cannabidiol who will benefit from treatment with fenfluramine according to the methods described herein.

Fenfluramine can then be employed to treat the patient either as a subsequent monotherapy or as a co-therapy with a second agent, such as cannabidiol. In some cases, the patient can be monitored for a reduction in instances of seizures (e.g., mean monthly convulsive seizures) relative to that observed under prior treatment with cannabidiol.

Fenfluramine can be administered in the form of the free base, or in the form of a pharmaceutically acceptable salt, for example selected from the group consisting of hydrochloride, hydrobromide, hydroiodide, maleate, sulphate, tartrate, acetate, citrate, tosylate, succinate, mesylate and besylate. Further illustrative pharmaceutically acceptable salts can be found in Berge et al., *J. Pharm. Sci.* (1977) 68(1): 1-19.

Fenfluramine for use in the methods of the present invention may be produced according to any pharmaceutically acceptable process known to those skilled in the art. Examples of processes for synthesizing fenfluramine are provided in the following documents: GB1413070, GB1413078, EP441160 and WO2017/112702.

The dose of fenfluramine to be used in a method of the present invention can be provided in the form of a kit, including instructions for using the dose in one or more of the methods of the present invention. In certain embodiments, the kit can additionally comprise a dosage form comprising one or more co-therapeutic agents.

A method of the present invention can be practiced on any appropriately diagnosed patient. In alternate exemplary embodiments of the present invention, the patient is aged about 30 or less, about 25 or less, about 20 or less, about 15 or less, about 10 or less, about 8 or less, about 6 or less or about 4 or less to about 10 months or more, about 4 months or more, about 6 months or more or about 1 year or more. Thus, in this embodiment, the diagnosed patient is about one month old to about 45 years old when treated.

The invention is further illustrated in the following Examples. The following examples are set forth to provide a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Add-on Therapy with Low Dose Fenfluramine (FFA) in Rett

The efficacy of fenfluramine as an add-on treatment in Rett patients is studied in an Investigator Initiated Study. The study design and protocol are described here.

Trial Objectives and Design

Design:

Open-Label Design:

Baseline Period (4 weeks): baseline seizure activity based on recordings of daily seizure activity entered into a diary.

Inclusions will be stratified by age group (≥4 to 10 years, >10 to 18 years) to ensure at least 30% of subjects will be in the group ≥4 to 10 years.

Titration Period (6 weeks): in 2-weeks increments starting with 0.2 mg/kg/day, then 0.5 mg/kg/day, and finally 0.8 mg/kg/day.

Maintenance Period (12 weeks): After completion of the Maintenance Period, eligible subjects will be offered enrollment in a separate open-label extension trial. Subjects who do not enroll in the open-label extension study will undergo a taper-off of study medication (doses will be administered similar to the titration, i.e., doses will be decreased in 2-weeks increments). Follow-up cardiovascular safety assessments, including ECG and ECHO, will be performed 3 to 6 months following the last dose of study medication.

An open-label, non-placebo controlled, add-on study is designed to assess the efficacy and safety of low-dose add-on fenfluramine across a range of fenfluramine doses (between 0.2 to 0.8 mg/kg/day, to a maximum of 30 mg/day) in between 15 and 20 Rett syndrome patients aged 4 to 18 years. The trial is conducted over an 18-week period, with responders eligible for follow-on treatment, with follow-up appointments at three-month intervals.

Inclusion and Exclusion Criteria

| Number of Subjects: 25-50 patients |
|---|
| Inclusion Criteria: |
| 1. Female, aged 4 to 18 years |
| 2. Clinical diagnosis of classic/typical Rett syndrome, with a documented mutation in the MECP2 gene. |
| 3. Convulsive seizures are not completely controlled by current antiepileptic drugs and subject must have had ≥6 main convulsive seizures (either tonic-clonic, tonic, clonic, myoclonic) per month for past 2 months prior to inclusion. |
| 4. A maximum of 2 current AEDs (ketogenic diet (KD) or vagal nerve stimulation (VNS) could be in addition). All medications or interventions for epilepsy (including KD and VNS) must be stable for at least 2 weeks prior to screening and are expected to remain stable throughout the study. |
| 5. Other medications frequently prescribed in Rett syndrome such as proton pump inhibitors and Vitamin D are permitted. |
| 6. Informed consent has been obtained from the legally responsible parent/guardian. |
| 7. Subject's parent/caregiver is willing and able to be compliant with diary completion, visit schedule and study drug accountability. |
| Exclusion Criteria: |
| 8. A known hypersensitivity to fenfluramine or any of the excipients in the study medication |

| Number of Subjects: 25-50 patients |
|---|
| 9. Pulmonary arterial hypertension, cardiac valvulopathy, myocardial infarction or stroke. |
| 10. Moderate or severe hepatic impairment. |
| 11. Concomitant therapy with: centrally-acting anorectic agents; monoamine-oxidase inhibitors; any centrally-acting compound with clinically appreciable amount of serotonin agonist or antagonist properties, including serotonin reuptake inhibition; atomoxetine, or other centrally-acting noradrenergic agonist; antiserotonergic agensts such as cyproheptadine, and/or cytochrome P450 (CYP) 2D6/3A4/2B6 inhibitors/substrates |
| 12. Subject has participated in another clinical trial within the past 30 days. |
| 13. Subject is currently receiving an investigational product. |
| Titration Inclusion Criteria: |
| 14. Subject does not have a cardiovascular or cardiopulmonary abnormality based on ECHO, ECG or physical examination, including but not limited to trace mitral or aortic valve regurgitation, or signs of pulmonary hypertension, and is approved for entry by the central cardiac safety reviewer. |
| 15. Subject demonstrates a stable baseline with ≥6 main motor seizures during the 4-week Baseline Period. |
| 16. Subject's parent/caregiver has been compliant with diary completion during the Baseline Period, in the opinion of the investigator (e.g., at least 90% compliant). |

Once enrolled, subjects are removed from the study in cases of serious adverse events, non-compliance, or lack of efficacy. Treatment is also stopped in the event of increased severity and frequency of seizures after discussion with the principle investigator; cardiac abnormalities (specifically, valvular problems), and/or adverse events (specifically, SAE, SAR or SUSAR) after discussion with the principle investigator. Patients may also withdraw voluntarily. Upon withdrawing, a safety examination (i.e., blood sampling and cardiac ultrasound) is performed and fenfluramine use is tapered for one week at 50% of end dosage and then withdrawn completely.

Trial Objectives

| Objectives: (Outcomes to be quantified and analyzed) |
|---|
| Primary objective: To show that Fenfluramine gives evidence of a treatment effect as open adjunctive therapy in the treatment of Rett syndrome in children and adolescents based on change in the frequency of the main motor seizures, stereotypies, respiratory dysfunction, and behavioral and emotional symptoms between baseline and the combined Titration and Maintenance Periods (T + M). |
| Secondary objectives: |
| Regarding seizures: |
| The proportion of subjects who achieve a ≥50% reduction from baseline in main convulsive seizure frequency. |
| The proportion of subjects who achieve ≥75% reductions from baseline in main convulsive seizure frequency. |
| The number of convulsive seizure-free days. |
| The change from baseline in each convulsive seizure type frequency. |
| The change from baseline in non-convulsive seizure frequency. |
| The incidence of rescue medication usage. |
| The incidence of hospitalization |
| The incidence of status epilepticus. |
| Regarding other neurological features |
| Motor and behavior symptoms: Rett Syndrome Behavior Questionnaire (RSBQ); including assessments of improvements in hand stereotypies, hyperventilation and breath holding |
| Rett syndrome Natural History Motor Behavior Assessment (MBA) (Total score, and MBA Modified Change Index) is more comprehensive and examines motor, behavior, and respiratory dysfunction(s) and, is intended to be a more dynamic measurement scale. The MBA incorporates measures of behavior/social assessment (range 0-64), orofacial/respiratory assessment (range 0-28), and motor assessment/ |

-continued

| Objectives: (Outcomes to be quantified and analyzed) |
|---|
| physical signs (range 0-56). Scores for all items are summed to obtain an overall score (range 0-148). In both measures, higher scores indicate more severe clinical status.<br>Clinician-Completed Domain-Specific Concerns VAS which uses a visual analog scale to assess domain-specific individualized symptoms that the investigating clinician identifies as key areas of impairment and may include six domains related to the subject's Rett syndrome: Repetitive Behaviors, Speech and Language, Anxiety, Social Withdrawal, Motor Performance, and Cognition.<br>Regarding the global Rett Syndrome condition:<br>Clinical Global Impression - Severity/Improvement (CGI-S, CGI-I) scores<br>assessed by the investigator<br>assessed by the parents:<br>Regarding safety:<br>adverse events<br>electrocardiograms (ECG, including QT duration),<br>echocardiograms (ECHO)<br>Weight and body mass index (BMI) |

Follow-up study: Responders at 20 weeks continue in a follow-up study, with visits scheduled at 3-month intervals. Patients receive a starting dose equal to the dosage received at week 20. At each visit, endpoints and safety criteria are assessed (seizure counting, current treatment, adverse effects, quality of life indicators (Clinical Global Impression of Improvement (CGI), sleep scale), pregnancy testing is performed, safety blood samples are collected, blood level AEDs are determined, and cardiac function is evaluated using EKG and cardiac ultrasound. Dosages may be increased as necessary, up to a maximum of 30 mg/day. Follow up ends when fenfluramine becomes available as a regular treatment or at the election of the patient and/or treating physician if serious side effects occur and/or the drug is no longer effective.

Additional endpoints to measure efficacy may include (but are not limited to):
  i. the proportion of subjects who achieve ≥25% reductions from baseline in convulsive seizure frequency.
  ii. the change from baseline in non-convulsive seizure frequency.
  iii. the change from baseline in convulsive+non-convulsive seizure frequency
  iv. the incidence of rescue medication usage
  v. the incidence of hospitalization to treat seizures
  vi. the incidence of status epilepticus
  vii. a comparison of the mean change in monthly convulsive seizure frequency between fenfluramine and placebo treatments over a treatment period compared with the baseline observation period.
  viii. the change in time to sleep onset and to sleep duration.
  ix. Changes in autonomic function, including breathing dysfunction, temperature dysregulation, peripheral vascular changes, enteric changes and cardiac abnormalities (including tachycardia, bradycardia, QTc interval abnormalities.
  x. Changes in aspects of behavioral dysregulation, such as generalized anxiety, phobias, panic attacks, mood liability, low mood, increasing hypersensitivity to sensory stimuli.

Materials and Methods

Ethics and regulatory approvals: Trial conduct complies with the most recent version of the principles of the Declaration of Helsinki, the principles of GCP, and in accordance with all applicable regulatory requirements. The study protocol and related documents is subject to ethical review by all requisite authorities. Participants have given written informed consent prior to their enrollment and participation in compliance with all applicable laws, regulations and ethical guidelines as required, and ICFs are retained at participating trial sites in accordance with all applicable regulatory agencies and laws. All information and data related to the Study and disclosed to the Participating Site and/or Study Investigator are treated as confidential and will not be disclosed to third parties or used for any purpose other than the performance of the study. Data collection, processing and disclosure of personal data is subject to compliance with applicable personal data protections and personal data processing requirements.

Fenfluramine: Oral fenfluramine hydrochloride solution (2.5 mg/ml or 5 mg/ml) is provided by Zogenix Pharma. Starting dosage is 0.2 mg/kg/day BID; second step at 0.4 mg/kg/day BID; maximum dosage at 0.8 mg/kg/day BID or 30 mg/day BID, whichever is less. The drug is dispensed by Zogenix Pharma. Labeled bottles containing the oral fenfluramine suspension is given to patients and controlled at each visit. Bottle labels are kept in individual patient files. Calculation of bottle number and control of labels are done at the trial's conclusion. Patient compliance is assessed by control of oral solution quantity at each visit and collection of seizure diary with notification of drug intake.

Concomitant treatment: Rett patients participating in the study may receive concomitant treatment up to two antiepileptic drugs commonly used in the treatment of the disorder. Maintenance of a ketogenic diet or vagal nerve stimulation may also be concomitant interventions. The drug regimen is must be stable for at least 2 weeks prior to screening with the expectation that they remain stable through the 18-week treatment period.

Laboratory tests: Blood analysis and urine pregnancy tests are done in central lab at UZ Leuven. Safety blood samples are tested for hemogram, electrolytes, liver function (SGOT, SGPT, LDH, PT) and kidney function (urea, creatinine)). AED blood level determination is limited to phenytoin, phenobarbital, carbamazepine, and valproate.

Safety assessment: Treatment safety is assessed using a combination of physical examination, blood testing, cardiac evaluation, and adverse event reporting. With respect to adverse event reporting, reporting is not required for expected AEs, moderate weight loss and decrease of appetite with no significant weight loss (<P3).

Data Handling and Statistical Analysis: Data is coded and is protected from disclosure outside of research teams according to the terms of the research protocol and the informed consent document. Subjects' names or other identifiers must be stored separately ("site file") from their research data and replaced with a unique code to create a new identify for the subject. Coded data are not anonymous. Data is collected in standardized CRF.

A priori data on possible efficacy is unavailable. Sample size is set at 20. The study is not randomized. Descriptive analysis of outcome parameters is done at weeks 8, 12, 16 and 20. All included subjects are counted for analysis. Reasons for withdrawal are documented.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of treating, preventing, and/or ameliorating seizures in a patient diagnosed with a mutation in cyclin-dependent kinase-like 5 (CDKL5) located in Xp22, the method comprising:
    administering a therapeutically effective dose of a formulation comprising fenfluramine or a pharmaceutically acceptable salt thereof, wherein the fenfluramine or the pharmaceutically acceptable salt thereof is formulated with a pharmaceutically acceptable carrier for administering an effective dose(s) of less than about 5.0 mg/kg/day to about 0.1 mg/kg/day.

2. The method of claim 1, wherein the method further comprises treating, preventing and/or ameliorating symptoms chosen from the group consisting of disordered breathing, autism spectrum behaviors, stereotypies, cognitive impairment, and sleep disturbances.

3. The method as claimed in claim 1, wherein the therapeutically effective dose is selected from the group consisting of 40 mg or less, 30 mg or less, and 20 mg or less, and wherein the therapeutically effective dose is administered in a dosage form selected from the group consisting of forms for oral, injectable, transdermal, inhaled, nasal, rectal, vaginal and parenteral delivery.

4. The method of claim 1, wherein fenfluramine is administered orally in an amount of between 0.2 mg/kg/day to 0.8 mg/kg/day, to a maximum of 30 mg/day.

5. The method as claimed in claim 4, wherein the method consists essentially of administering the therapeutically effective dose of the formulation consisting essentially of the fenfluramine and the pharmaceutically acceptable carrier to the patient diagnosed with the mutation in cyclin-dependent kinase-like 5 (CDKL5) located in Xp22.

6. The method as claimed claim 4, wherein the fenfluramine is co-administered with one or more co-therapeutic anti-epileptic agents selected from the group consisting of carbamazepine, ethosuximide, fosphenytoin, lamotrigine, levetiracetam, phenobarbital, topiramate, stiripentol, valproic acid, valproate, verapamil, vigabatrin and benzodiazepines such as clobazam, clonazepam, diazepam, lorazepam, and midazolam and a pharmaceutically acceptable salt or base thereof.

7. The method as claimed in claim 4, wherein the fenfluramine is co-administered with one or more co-therapeutic agents selected from the group consisting of LM22A-4, fingolimod, copaxone, CX-546, 5-FPT, 7,8-dihydroxyflavone, R7, R13, LP-211, clenbuterol, IGF-1; trofenatide, NLX-101, sarizotan, ketamine, NO-711, lovastatin, corticoseterone, CNF1, triheptanoin, EPI-732, benserazide, L-DOPA, citalopram and mecanserin.

8. The method as claimed in claim 4, wherein the fenfluramine is co-administered with stiripentol as a co-therapeutic agent.

9. The method of claim 8, wherein the stiripentol is administered in an amount sufficient to increase fenfluramine blood levels by 50% or more relative to fenfluramine blood levels obtained in the absence of the co-administration of the stiripentol, and further wherein blood levels of a metabolite of fenfluramine are decreased relative to levels of the fenfluramine metabolite obtained in the absence of the co-administration of the stiripentol.

10. A method of ameliorating seizures in a patient with a mutation in cyclin-dependent kinase-like 5 (CDKL5) located in Xp22, the method comprising:
    diagnosing the patient as having the mutation in cyclin-dependent kinase-like 5 (CDKL5) located in Xp22;
    administrating to the patient a therapeutically effective dose of fenfluramine or a pharmaceutically acceptable salt thereof;
    thereby ameliorating seizures in the patient.

11. The method of claim 10, wherein the method further comprises ameliorating further symptoms selected from the group consisting of disordered breathing, autism spectrum behaviors, stereotypies, cognitive impairment, and sleep disturbances.

12. The method of claim 10, wherein fenfluramine is administered orally in an amount between 0.2 mg/kg/day and 0.8 mg/kg/day, to a maximum of 30 mg/day.

13. The method of claim 12, wherein the method consists essentially of administering the therapeutically effective dose of the formulation consisting essentially of the fenfluramine and the pharmaceutically acceptable carrier to the patient diagnosed with the mutation in cyclin-dependent kinase-like 5 (CDKL5) located in Xp22.

14. The method of claim 12, wherein the effective dose of the fenfluramine is co-administered with one or more co-therapeutic anti-epileptic agents selected from the group consisting of carbamazepine, ethosuximide, fosphenytoin, lamotrigine, levetiracetam, phenobarbital, topiramate, stiripentol, valproic acid, valproate, verapamil, vigabatrin and benzodiazepines such as clobazam, clonazepam, diazepam, lorazepam, and midazolam and a pharmaceutically acceptable salt or base thereof.

15. The method of claim 12, wherein the fenfluramine is administered with a co-therapeutic agent is selected from the group consisting of stiripentol, and a combination of both.

16. The method of claim 14, wherein the one or more co-therapeutic anti-epileptic agents are selected from vigabatrin, clobazam, valproic acid and lamotrigine.

17. The method of claim 10, wherein the effective dose is 20 mg or less.

* * * * *

UNITED STATES PATENT AND TRADEMARK OFFICE
CERTIFICATE OF CORRECTION

PATENT NO. : 12,144,787 B2
APPLICATION NO. : 17/289125
DATED : November 19, 2024
INVENTOR(S) : Bradley S. Galer et al.

It is certified that error appears in the above-identified patent and that said Letters Patent is hereby corrected as shown below:

On the Title Page

In Column 1, under "Prior Publication Data", Line 2, below "Jan. 13, 2022" insert -- Related U.S. Application Data (60) Provisional application No. 62/769,441, filed on November 19, 2018. --, as a new field entry.

In the Specification

In Column 2, Line 38, delete "Neuropaediatrics," and insert -- Neuropediatrics, --.

In Column 7, Line 57, delete "BNDF." and insert -- BDNF. --.

In Column 7, Line 67, delete "Mecanserin and trofenatide" and insert -- Ketanserin and trofinetide --.

In Column 8, Line 14, delete "Avanex2-73)" and insert -- Anavex2-73) --.

In Column 9, Line 50, delete "5-HT$_{5B}$" and insert -- 5-HT$_{5B}$, --.

In Column 9, Line 66, delete "vigabtrin" and insert -- vigabatrin --.

In Column 10, Line 67, delete "and or" and insert -- and/or --.

In Column 11, Line 31, delete "HT$_{2C}$" and insert -- 5-HT$_{2C}$ --.

In Column 11, Line 44, delete "trofenatide," and insert -- trofinetide, --.

In Column 11, Lines 45-46, delete "corticoseterone," and insert -- corticosterone, --.

In Column 11, Line 47, delete "mecanserin." and insert -- ketanserin. --.

Signed and Sealed this
Eleventh Day of March, 2025

Coke Morgan Stewart
*Acting Director of the United States Patent and Trademark Office*

CERTIFICATE OF CORRECTION (continued)
U.S. Pat. No. 12,144,787 B2

In Column 11, Line 57, delete "flenfluramine" and insert -- fenfluramine --.

In Column 15, Line 39, delete "sialastic" and insert -- silastic --.

In Column 15, Line 50, delete "(c)" and insert -- (d) --.

In Column 17, Lines 52-53, delete "and or" and insert -- and/or --.

In Column 18, Line 29, delete "and ore or" and insert -- and/or --.

In Column 19, Line 19, delete "the a" and insert -- a --.

In Column 19, Line 38, after "decline" insert -- . --.

In Column 30, Line 12, delete "agensts" and insert -- agents --.

In the Claims

In Column 33, Line 49, in Claim 6, after "claimed" insert -- in --.

In Column 34, Line 2, in Claim 7, delete "trofenatide," and insert -- trofinetide, --.

In Column 34, Lines 3-4, in Claim 7, delete "corticoseterone," and insert -- corticosterone, --.

In Column 34, Line 5, in Claim 7, delete "mecanserin." and insert -- ketanserin. --.